(12) United States Patent
Kobayashi et al.

(10) Patent No.: US 7,282,316 B2
(45) Date of Patent: Oct. 16, 2007

(54) SULFONYLDIAZOMETHANE COMPOUNDS, PHOTOACID GENERATOR, RESIST MATERIALS AND PATTERNING USING THE SAME

(75) Inventors: Katsuhiro Kobayashi, Niigata-ken (JP); Youichi Ohsawa, Niigata-ken (JP); Takeshi Kinsho, Niigata-ken (JP); Eiji Fukuda, Niigata-ken (JP); Shigeo Tanaka, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/929,059

(22) Filed: Aug. 27, 2004

(65) Prior Publication Data

US 2005/0048395 A1    Mar. 3, 2005

(30) Foreign Application Priority Data

Aug. 28, 2003   (JP)   ............... 2003-304060

(51) Int. Cl.
G03F 7/004 (2006.01)
G03F 7/30 (2006.01)

(52) U.S. Cl. .................. 430/170; 430/270.1; 430/326; 430/330; 430/905; 430/910; 534/558

(58) Field of Classification Search ............... 430/170, 430/270.1, 905, 910, 326, 330; 534/558
See application file for complete search history.

(56) References Cited

U.S. PATENT DOCUMENTS

| 2,354,229 | A |   | 7/1944  | Walter |   |
|---|---|---|---|---|---|
| 5,216,135 | A | * | 6/1993  | Urano et al. | 534/556 |
| 5,945,517 | A | * | 8/1999  | Nitta et al. | 534/558 |
| 6,004,724 | A |   | 12/1999 | Yamato et al. |   |
| 6,261,738 | B1 |  | 7/2001  | Asakura et al. |   |
| 6,338,931 | B1 | * | 1/2002 | Maeda et al. | 430/170 |
| 6,395,446 | B1 | * | 5/2002 | Seki et al. | 430/170 |

FOREIGN PATENT DOCUMENTS

| JP | 3-103854 | 4/1991 |
|---|---|---|
| JP | 4-211258 | 8/1992 |
| JP | 8-123032 | 5/1996 |
| JP | 9-95479 | 4/1997 |
| JP | 9-208554 | 8/1997 |
| JP | 9-230588 | 9/1997 |
| JP | 9-301948 | 11/1997 |
| JP | 10-90884 | 4/1998 |
| JP | 11-38604 | 2/1999 |
| JP | 11-72921 | 3/1999 |
| JP | 2906999 | 4/1999 |
| JP | 11-190904 | 7/1999 |
| JP | 3024621 | 1/2000 |
| JP | 2000-314956 | 11/2000 |
| JP | 2000-344836 | 12/2000 |
| JP | 2001-55373 | 2/2001 |
| JP | 2001-106669 | 4/2001 |

OTHER PUBLICATIONS

Paquette, "A Facile Conversion of Mercaptans to Homologous Terminal Olefins," *J. Am. Chem. Soc.*, vol. 86, pp. 4383-4385, Oct. 20, 1964.
Walter et al., "Thioether Barbiturates. I. Thiomethyl Derivatives," *J. Am. Chem. Soc.*, vol. 67, pp. 655-659, Apr. 1945.
Arimitsu et al., "Sensitivity Enhancement of Chemical-Amplification-Type Photoimaging Materials by Acetoacetic Acid Derivatives," *J. Photopolym. Sci. and Tech.*, vol. 8, No. 1, pp. 43-44, May 1995.
Arimitsu et al., "Effect of Phenolic Hydroxyl Residues on the Improvement of Acid-Proliferation-Type Photoimaging Materials,," *J. Photopolym. Sci. and Tech.*, vol. 9, No. 1, pp. 29-30, May. 1996.
Kudo et al., "Enhancement of the Sensitivity of Chemical-Amplification-Type Photoimaging Materials by B-Tosyloxyketone Acetals," *J. Photopolym. Sci. and Tech.*, vol. 8, No. 1, pp. 45-46, May 1995.

* cited by examiner

*Primary Examiner*—John S. Chu
(74) *Attorney, Agent, or Firm*—Alston & Bird LLP

(57) ABSTRACT

Provided are sulfonyldiazomethane compounds and photo-acid generators suited for resist materials which generate less foreign matters after application, development and peeling, and in particular, are excellent in the pattern profile after the development; and resist materials and patterning process using them. Provided are sulfonyldiazomethane compounds represented by formula (1):

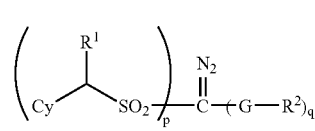

Also provides are photoacid generators containing the sulfonyldiazomethane compounds, and a chemical amplification resist material comprising (A) a resin which changes its solubility in an alkali developer by action of an acid, and (B) a sulfonyldiazomethane compound of formula (1) capable of generating an acid by exposure to radiation. Provided is a patterning process comprising steps of applying the above-described resist material onto a substrate to form a coating, heating the coating, exposing the coating, and developing the exposed coating in a developer after an optional heat treatment.

20 Claims, No Drawings

SULFONYLDIAZOMETHANE COMPOUNDS, PHOTOACID GENERATOR, RESIST MATERIALS AND PATTERNING USING THE SAME

CROSS-REFERENCE TO RELATED APPLICATIONS

The present application claims priority to Japanese Patent Application No. 2003-304060, filed Aug. 28, 2003, the disclosure of which is incorporated herein by reference in its entirely.

BACKGROUND OF THE INVENTION

1. Field of the Invention

This invention relates to sulfonyldiazomethane compounds suited for chemical amplification resist materials for the fabrication of integrated circuits or the other electronic devices which are sensitive to radiation such as UV, deep UV, electron beams, x-rays, excimer laser beam, γ-rays, and synchrotron radiation; photoacid generators for resist materials; and resist materials comprising the sulfonyldiazomethane, and a patterning process using the material.

2. Description of the Related Art

As a finer pattern rule is requested in the trend of higher integration and higher speed of LSI, deep-ultraviolet lithography is regarded promising as a microfabrication technology of next generation.

In recent days, technology making use of, as a deep UV light source, a high-luminosity KrF excimer laser, especially an Ar F excimer laser featuring a shorter wavelength has attracted attentions. In order to deal with a decrease in the wavelength of an exposure light and heightening in the resolution of a resist material, there is a demand for the development of more improved microfabrication technology.

From such viewpoints, chemical amplification resist materials which have been developed recently and employ an acid as a catalyst are particularly promising resist materials for deep UV lithography, because they have excellent features such as high sensitivity, resolution and dry etching resistance. The chemical amplification resist materials can be classified into positive type in which unexposed areas remain by the removal of exposed areas and negative type in which the exposed areas remain by the removal of unexposed areas.

In chemical amplification positive resist materials to be developed with an alkaline developer, a resin and/or compound have part or all of the alkali soluble phenol or carboxylic acid protected with a substituent (acid-labile group) capable of changing the solubility of the resin and/or compound in an alkali developer by the action of an acid. It is catalytically decomposed by an acid generated upon exposure and the exposed area on which phenol or carboxylic acid has been generated is removed by the alkaline developer. In chemical amplification negative resist materials, a resin and/or compound having an alkali-soluble phenol or carboxylic acid and a compound (acid crosslinking agent) capable of bonding (crosslinking) the resin or compound under the action of an acid are crosslinked by an acid generated upon exposure, whereby the exposed area is made insoluble in the alkali developer and the unexposed area is removed by the alkaline developer.

In the chemical amplification positive resist materials, a resist film is formed by dissolving a binder resin having an acid-labile group and a compound capable of generating an acid upon exposure to radiation (which will hereinafter be referred to as "photoacid generator") in a solvent, applying the resultant resist solution onto a substrate by any one of a variety of methods, heating if necessary, and evaporating off the solvent. The resist film is then exposed to radiation, for example, deep UV as a light source through a predetermined mask pattern. The exposed resist film is then optionally subjected to post exposure bake (PEB) in order to promote catalytic reaction with an acid, followed by development with an aqueous alkaline solution to remove the resist film from the exposed area, whereby a positive pattern profile is obtained. After the substrate is etched by any one of various methods, the remaining resist film is removed by dissolution in a remover solution or ashing to form a desired pattern profile on the substrate.

For the chemical amplification positive resist materials for KrF excimer laser, a phenolic resin such as polyhydroxystyrene having part or all of the hydrogen atoms of the phenolic hydroxyl groups protected with an acid-labile protective group have been used. As the photoacid generator, iodonium salt, sulfonium salt, or bissulfonyldiazomethane has been used. If necessary, a carboxylic acid and/or phenol derivative having a molecular weight not greater than 3,000 and having part or all of the carboxylic acid and/or phenolic hydroxyl groups protected with an acid-labile group, which serves as a dissolution inhibiting or promoting compound; a carboxylic acid compound for improving dissolution properties; a basic compound for improving contrast; and a surfactant for improving application properties are added.

Bissulfonyldiazomethanes as shown below are suited for use as a photoacid generator of chemical amplification resist materials, especially chemical amplification positive resist materials for KrF excimer laser, because they are excellent in sensitivity and resolution, and are superior in compatibility with resins and solubility in resist solvents over sulfonium salt or iodonium salt photoacid generators, as disclosed in Japanese Patent No. 3024621 or Japanese Patent Application Unexamined Publication No. 3-103854/1991.

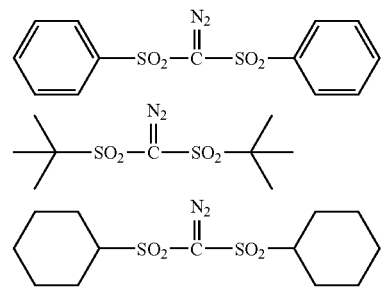

Sulfonyldiazomethanes having aryl groups, however, show a large absorption in a deep UV wavelength region and a high content thereof lowers transparency of the resist film itself, leading to deterioration in the pattern shape. When a diazomethane having the alkyl group instead of the aryl group is used, an acid having a relatively low molecular weight is generated, which tends to lower resolution owing to a large diffusion of it in the resist film. When it is added in a larger amount, the problem of an insoluble matter upon development and/or removal of the resist film cannot be overcome owing to the high crystallinity of the compound itself.

The positive resist material comprising a disulfonyldiazomethane having an acid-labile group such as tert-butoxycarbonyloxy group, ethoxyethyl group or tetrahydropyranyl group in order to improve contrast is also proposed in Japanese Patent Application Unexamined Publication No. 10-90884/1998. According to the investigation by the present inventors, however, such a compound lacks stability.

The present inventors have already synthesized a sulfonyldiazomethane having an acyl group such as acetyl or a methanesulfonyl group introduced therein and used it as a photoacid generator of a chemical amplification resist material. The acyl or methanesulfonyl-substituted arylsulfonyldiazomethane, however, lacks stability under basic conditions. Moreover, their absorption in the deep UV is strong owing to the aryl group in the molecule so that addition of a large amount thereof lowers transparency of the resist film itself (Japanese Patent-Application Unexamined Publication Nos. 2001-55373 and 2001-106669).

Combination of two or more photoacid generators for a resist material is a technique already disclosed in Japanese Patent Application Unexamined Publication No. 8-123032/1996. It is reported in Japanese Patent Application Unexamined Publication No. 11-72921/1999 that incorporation of a radiation-sensitive photoacid generator comprising a mixture of a compound which generates a three-or-more-fluorine-containing sulfonic acid by exposure to radiation and a compound which generates a fluorine-free sulfonic acid by exposure to radiation improves resolution without causing nano edge roughness or film surface roughness; or in Japanese Patent Application Unexamined Publication No. 11-38604/1999 that a resist material comprising an asymmetric bissulfonyldiazomethane such as a bissulfonyldiazomethane having alkylsulfonyl and arylsulfonyl groups or a bissulfonyldiazomethane having arylsulfonyl and alkoxy-substituted arylsulfonyl groups, and a polymer of a polyhydroxystyrene derivative having an acid-labile group has resolution at least equal to conventional materials, a sufficient sensitivity and significantly excellent heat resistance. According to the investigation by the present inventors, however, these resist materials are unsatisfactory in resolution and from the synthetic and industrial standpoints, asymmetric bissulfonyldiazomethanes have drawbacks.

When the time from exposure to post-exposure baking (PEB) (PED: post-exposure delay) is prolonged, a change in pattern profile tends to occur. In a chemical amplification positive resist material using an acid-labile group such as acetal, it appears as a thinned line width of unexposed areas, while in a chemical amplification positive resist material using an acid-labile group such as tert-butoxycarbonyl (t-BOC), it appears as a thickened line width of unexposed areas. The period from exposure to PEB is sometimes prolonged for the operational reason so that there is a demand for stable resist materials not causing such a change, that is, a resist material having good PED stability.

The solubility of a photosensitizing agent or photoacid generator has been regarded as a problem since quinonediazide was used as a photosensitizing agent for non-chemical amplification resist materials. More specifically, the problems involve the solubility of a photoacid generator in resist solvent, the compatibility between the photoacid generator and resin, the solubility in (or affinity with) a developer of photo-decomposed products and the photo-undecomposed compound (photoacid generator) after exposure and PEB, and the solubility of the photoacid generator in a remover solvent upon resist removal (peeling). Poor solubility presumably causes precipitation of the photoacid generator during storage, difficulty in filtration, uneven coating, striation, abnormal resist sensitivity, and appearance of foreign matters, dissolution residues or stains on the pattern or in the space after development.

SUMMARY OF THE INVENTION

The photoacid generator of a resist material is required to have a sufficiently high solubility in (or compatibility with) a resist solvent and a resin, good storage stability, no toxicity and good application properties, not to generate foreign matters upon pattern formation after development and upon resist peeling, and have a good pattern profile and high PED stability. The conventional photoacid generators, especially diazodisulfone ones do not satisfy all of these requirements.

An object of the invention is to overcome the above-described various problems and at the same time, to provide a sulfonyldiazomethane compound and a photoacid generator suited for use in a resist material, particularly a chemical amplification resist material, which leaves less foreign matters after application, development and peeling and, in particular, is excellent in the pattern profile after development; and a resist material and patterning process using these compounds.

The present inventors have carried out an extensive investigation with a view to attaining the above-described object. As a result, it has been found that a resist material comprising, as a photoacid generator, a sulfonyldiazomethane compound represented by formula (1) below, has excellent solubility, storage stability and applicability, less change in the line width and less shape deterioration even if PED lasts for long hours. It has been also found that the resist material leaves less foreign matters after application, development and peeling, is excellent in pattern profile after the development, has high resolution suited for microfabrication, and exhibits great advantages especially in deep UV lithography.

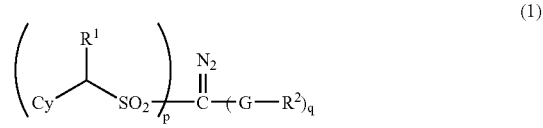

(1)

wherein $R^1$ represents a hydrogen atom or a linear, branched or cyclic, substituted or unsubstituted $C_{1-6}$ alkyl group; Cy represents a cyclohexyl group, a cyclohexyl group having part or all of the hydrogen atoms in a ring thereof substituted by a linear, branched or cyclic, substituted or unsubstituted $C_{1-6}$ alkyl or alkoxy group, a cyclohexyl group having a carbonyl group in a ring thereof, a cyclohexyl group having a carbonyl group in a ring thereof and having part or all of the hydrogen atoms in the ring substituted by a linear, branched or cyclic, substituted or unsubstituted $C_{1-6}$ alkyl or alkoxy group, or a cyclohexyl group with a $C_{0-6}$ alicyclic or heterocyclic structure; G represents $SO_2$ or CO; $R^2$ represents a linear, branched or cyclic, substituted or unsubstituted $C_{1-10}$ alkyl group or a substituted or unsubstituted $C_{6-14}$ aryl group; and p stands for 1 or 2 and q stands for 0 or 1, satisfying p+q=2.

It has been found that when a sulfonyldiazomethane compound represented by formula (1) is used as a photoacid generator of a chemical amplification resist material such as a chemical amplification positive resist material comprising a resin which changes its solubility in an alkaline developer by the cleavage of a C—O—C bond through action of an acid, the resulting resist material is excellent in the above-described effects, particularly it exerts its effects greatly in deep UV lithography, leading to the completion of the invention.

The invention provides a sulfonyldiazomethane compound represented by formula (1) and a photoacid generator comprising the sulfonyldiazomethane compound. The invention also provides a chemical amplification resist material comprising (A) a resin which changes its solubility in an alkali developer by action of an acid; and (B) a sulfonyldiazomethane compound of formula (1) capable of generating an acid by exposure to radiation. It also provides a patterning process comprising steps of applying the resist material onto a substrate to form a coating, heating the resulting coating, exposing the heat-treated coating to high energy radiation having a wavelength not greater than 300 nm or electron beam through a photomask, and developing the exposed coating with a developer after an optional heat treatment.

According to the invention, the sulfonyldiazomethane and the chemical amplification resist material comprising sulfonyldiazomethane have excellent resolution and focus latitude, less change in line width and less deterioration in shape even after long PED, leave less foreign matters after application, development and peeling, have excellent pattern profile after the development, and have high resolution suited for microfabrication. They exert particularly high effects in deep UV lithography. It is because the sulfonyldiazomethane contains a long-chain alkylcyclohexyl group.

DETAILED DESCRIPTION OF THE PREFERRED EMBODIMENTS

The invention will hereinafter be described more specifically.

Firstly, according to the invention, there is thus provided a novel sulfonyldiazomethane compound represented by formula (1). As the sulfonyldiazomethane compound of formula (1), sulfonyldiazomethane compounds of any one of the below-described formulas (1a), (1a') and (1a'') having an alkylcyclohexylmethyl group may be particularly preferred.

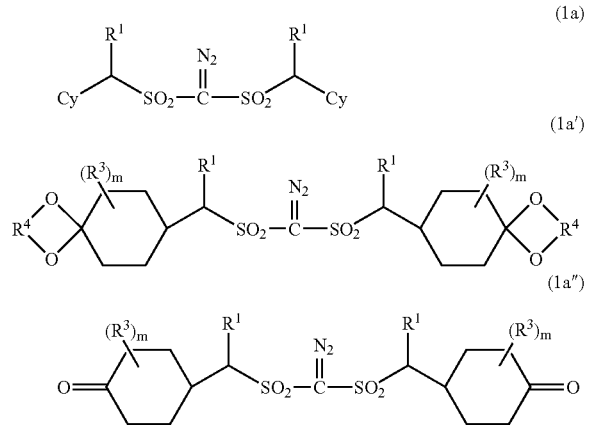

In the above-described formulas, $R^1$s may be same or different, $R^3$s may be same or different and each represents a hydrogen atom or a linear, branched or cyclic, substituted or unsubstituted $C_{1-6}$ alkyl group or a plurality of $R^3$s may be coupled to form an alicyclic hydrocarbon structure or heterocyclic structure having from 6 to 12 carbon atoms including the carbon atoms to which they are bonded, m stands for an integer of from 0 to 9, and $R^4$s may be same or different and each represents a linear or branched $C_{2-6}$ alkylene group.

In the above-described formulas (1), (1a), (1a') and (1a''), $R^1$s may be same or different and each represents a hydrogen atom or a linear, branched or cyclic, substituted or unsubstituted $C_{1-6}$ alkyl group.

Specific examples include, but not limited to, a hydrogen atom and methyl, ethyl, n-propyl, isopropyl, cyclopropyl, n-butyl, sec-butyl, isobutyl, tert-butyl, n-pentyl, sec-pentyl, isopentyl, tert-pentyl, neopentyl, n-hexyl, isohexyl and thexyl groups, and the above-described alkyl groups having part or all of the hydrogen atoms substituted by a halogen atom such as chlorine or fluorine. Of these, a hydrogen atom, and methyl, ethyl, n-propyl, isopropyl and n-butyl groups are preferred, with a hydrogen atom being more preferred.

Cy represents a cyclohexyl group, a cyclohexyl group having part or all of the hydrogen atoms in the ring thereof substituted by a linear, branched or cyclic, substituted or unsubstituted $C_{1-6}$ alkyl or alkoxy group, a cyclohexyl group having a carbonyl group in the ring thereof, a cyclohexyl group having a carbonyl group in the ring thereof and having part or all of the hydrogen atoms, in the ring, substituted by a linear, branched or cyclic, substituted or unsubstituted $C_{1-6}$ alkyl or alkoxy group, or a cyclohexyl group with a $C_{0-6}$ alicyclic or heterocyclic structure.

Of these, $C_{10-18}$ cyclohexyl groups are preferred, because when the number of carbon atoms is small, an acid generated may have a relatively low molecular weight and may not contribute to dissolve the diffusion problem in the resist film, while a large number of carbon atoms may lead to a problem in synthesis such as too high boiling point of a raw material thiol. Cyclohexyl groups having 10 to 12 carbon atoms are more preferred. In addition, a cyclohexyl group with a ketalic carbon is preferred in order to reduce foreign matters upon patterning after development and upon resist removal.

Specific examples of Cy include, but not limited to, cyclohexyl groups substituted by a linear, branched or cyclic alkyl group such as methylcyclohexyl, ethylcyclohexyl, n-propylcyclohexyl, isopropylcyclohexyl, n-butylcyclohexyl, sec-butylcyclohexyl, isobutylcyclohexyl, tert-butylcyclohexyl, n-pentylcyclohexyl, sec-pentylcyclohexyl, cyclopentylcyclohexyl, n-hexylcyclohexyl, and cyclohexylcyclohexyl; cyclohexyl groups substituted by a linear, branched or cyclic alkoxy group such as methoxycyclohexyl, ethoxycyclohexyl, n-propoxycyclohexyl, n-butyloxycyclohexyl, n-pentyloxycyclohexyl, neopentyloxycyclohexyl, n-hexyloxycyclohexyl, cyclopentyloxycyclohexyl, cyclohexyloxycyclohexyl, methoxymethylcyclohexyl, ethoxymethylcyclohexyl, dimethoxycyclohexyl, diethoxycyclohexyl, and 1,3-dioxolan-2-ylcyclohexyl; cyclohexyl groups having in the ring thereof a carbonyl group such as oxocyclohexyl; and cyclohexyl group with an alicyclic hydrocarbon structure such as bicyclo[2.2.1]heptyl. In the alkyl group of the above-described cyclohexyl groups, part or all of the hydrogen atoms may be substituted with a halogen atom such as chlorine or fluorine. Of these, tert-butylcyclohexyl, 1,3-dioxolan-2-ylcyclohexyl and oxycyclohexyl groups are preferred.

$R^2$ represents a linear, branched or cyclic, substituted or unsubstituted $C_{1-10}$ alkyl group or a substituted or unsubstituted $C_{6-14}$ aryl group.

Specific examples of $R^2$ include, but not limited to, linear, branched or cyclic alkyl groups such as methyl, ethyl, n-propyl, isopropyl, n-butyl, sec-butyl, isobutyl, tert-butyl, n-pentyl, sec-pentyl, cyclopentyl, n-hexyl, and cyclohexyl, aryl groups such as phenyl, 4-methylphenyl, 4-ethylphenyl, 4-methoxyphenyl, 4-tert-butylphenyl, 4-tert-butoxyphenyl, 4-cyclohexylphenyl, 4-cyclohexyloxyphenyl, 2,4-dimethylphenyl, 2,4,6-trimethylphenyl, 2,4,6-triisopropylphenyl, 1-naphthyl, and 2-naphthyl, and the above-described alkyl or aryl groups having part or all of the hydrogen atoms substituted by a halogen such as chlorine or fluorine. Of these, tert-butyl and cyclohexyl groups are preferred.

$R^3$s may be same or different and each represents a hydrogen atom, or a linear, branched or cyclic, substituted or unsubstituted $C_{1-6}$ alkyl group.

Specific examples of $R^3$ include, but not limited to, a hydrogen atom, and linear, branched or cyclic alkyl groups such as methyl, ethyl, n-propyl, isopropyl, n-butyl, sec-butyl, isobutyl, tert-butyl, n-pentyl, sec-pentyl, cyclopentyl, n-hexyl and cyclohexyl groups. Of these, a hydrogen atom and methyl group are preferred.

Alternatively, a plurality of $R^3$ may be coupled together to form an alicyclic hydrocarbon structure or a heterocyclic structure having 6 to 12 carbon atoms including the carbon atoms to which $R^3$s are bonded. Specific examples include, but not limited to, methylene and ethylene. The letter m stands for an integer of from 0 to 9.

$R^4$ represents a linear or branched $C_{2-6}$ alkylene group.

Specific examples of $R^4$ include, but not limited to, linear or branched alkylene groups such as ethylene, trimethylene, 2,2-dimethyltrimethylene, propylene, tetramethylene, pentamethylene and hexamethylene. Of these, ethylene group is preferred.

G means $SO_2$ or CO, of which $SO_2$ is preferred.

The letter p stands for 1 or 2 and q stands for 0 or 1, satisfying p+q=2.

A process for synthesizing the above-described sulfonyldiazomethane will next be described, but not limited thereto.

When p=2, that is, the sulfonyldiazomethane is a symmetric bissulfonyldiazomethane, it is desired to react a corresponding thiol with dichloromethane for condensation under a basic condition as disclosed in Japanese Patent Application Unexamined Publication No. 3-103854/1991. More specifically, an alkyl-containing thiol such as cyclohexylmethanethiol is reacted with dichloromethane for condensation in an alcohol solvent such as methanol or ethanol in the presence of a base such as sodium hydroxide or potassium hydroxide to obtain a sulfenylmethane.

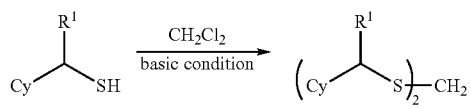

Herein Cy has the same meaning as described above.

Alternatively, thiol can be reacted with paraformaldehyde for condensation under an acidic condition such as sulfuric acid or trifluoromethanesulfonic acid.

When p=1, that is, the sulfonyldiazomethane is an asymmetric sulfonyldiazomethane, a halomethylthioether is reacted with a cyclohexylmethanethiol. Upon preparation of sulfonylcarbonyldiazomethane, α-halomethylketone is reacted with cyclohexylmethanethiol. The halomethyl thioether is available from a corresponding thiol, formaldehyde and hydrogen chloride (J. Am. Chem. Soc., 86, 4383(1964), J. Am. Chem. Soc., 67, 655 (1945), and U.S. Pat. No. 2,354,229).

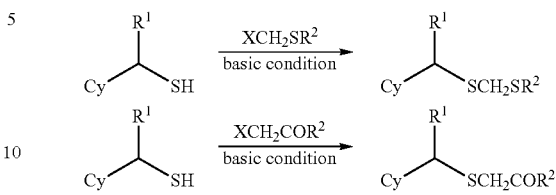

Herein Cy and $R^2$ have the same meanings as described above.

Further, each product thus obtained is oxidized with an oxidizing agent such as aqueous hydrogen peroxide in the presence of sodium tungstate, as described in Japanese Patent Application Unexamined Publication No. 4-211258/1992, whereby a corresponding sulfonylmethane is obtained.

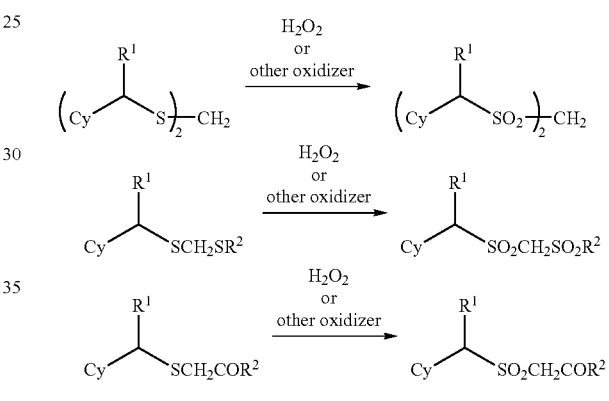

Herein Cy and $R^2$ have the same meanings as described above.

The sulfonylmethane is then diazotized with p-toluenesulfonylazide, p-dodecylbenzenesulfonylazide or p-acetamidobenzenesulfonylazide under a basic condition to obtain the intended sulfonyldiazomethane.

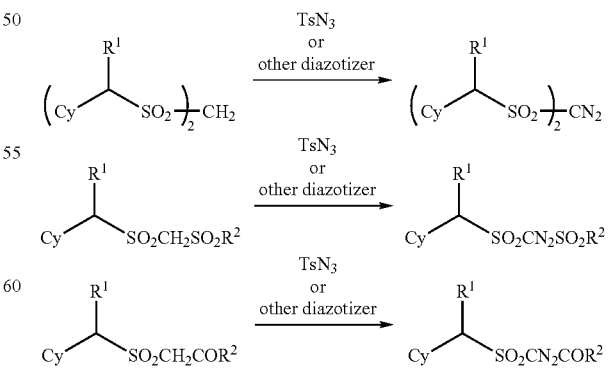

Herein Cy and $R^2$ have the same meanings as described above.

Although no particular limitation is imposed on the synthesis of cyclohexylmethanethiol, it can be synthesized, for example, by adding thioacetic acid to an olefin, followed by hydrolysis.

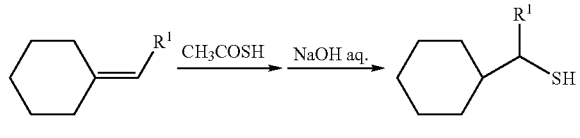

Herein R¹ has the same meaning as described above.

Although no particular limitation is imposed on the synthesis of alkenylidenecyclohexane, it can be synthesized, for example, by Wittig reaction or Peterson reaction from the corresponding cyclohexanone.

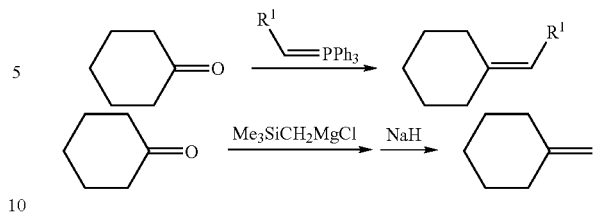

Herein R¹ has the same meaning as described above.

Examples of the sulfonyldiazomethane of the invention represented by formula (1) or formula (1a), (1a') or (1a") include, but not limited to, compounds having the below-described structure.

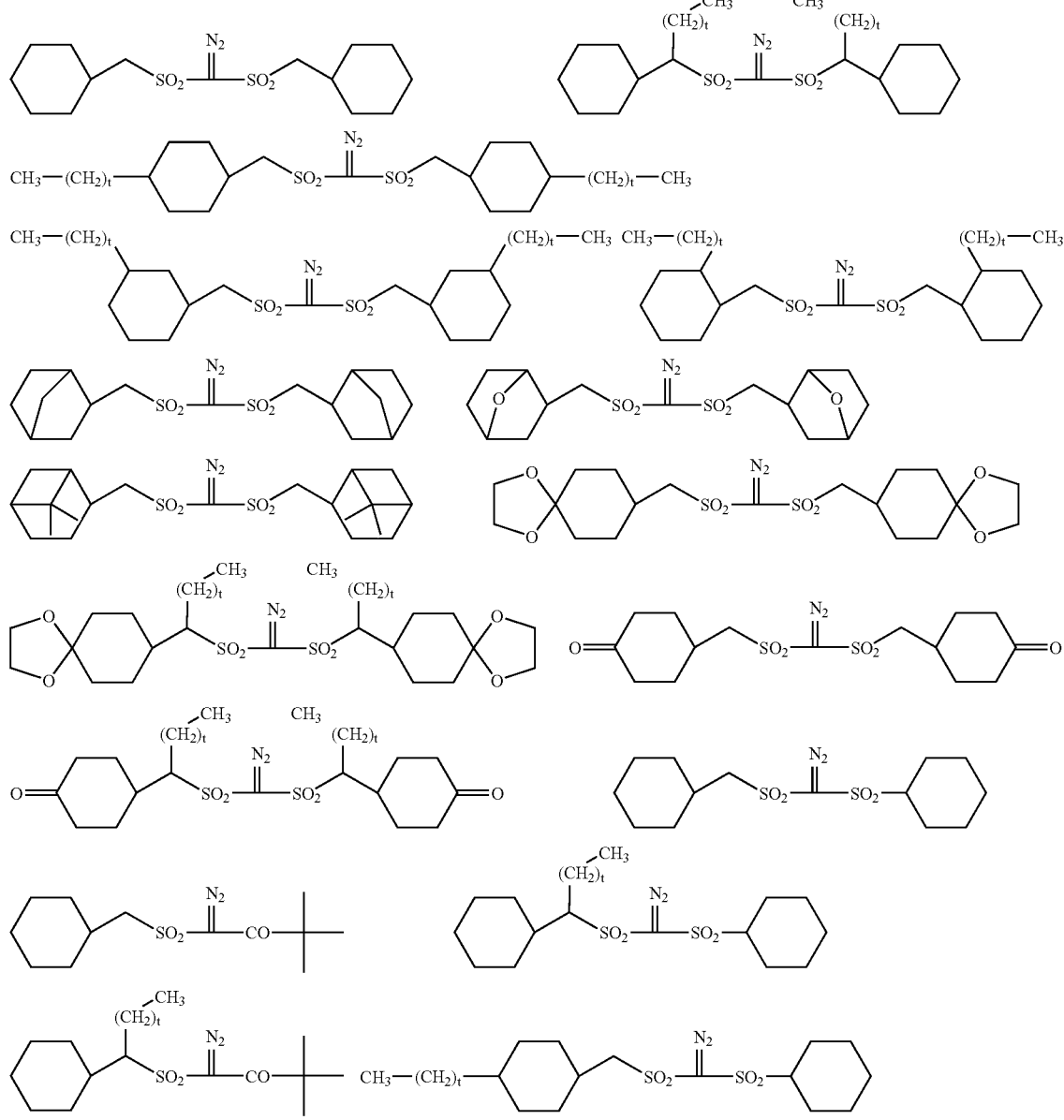

-continued

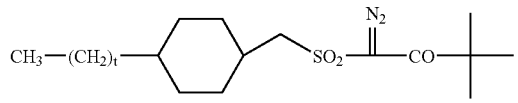
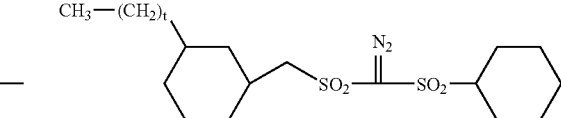

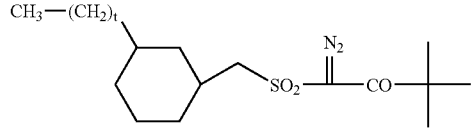
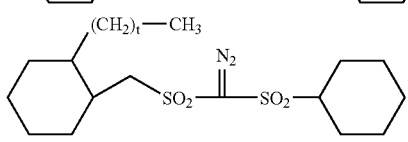

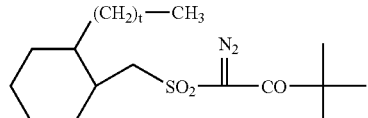
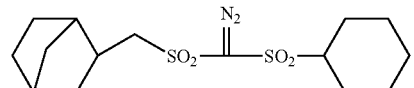

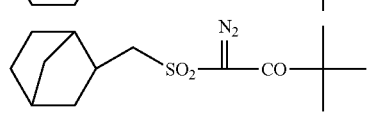
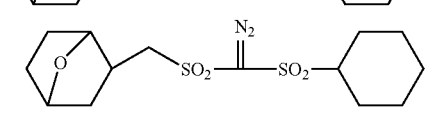

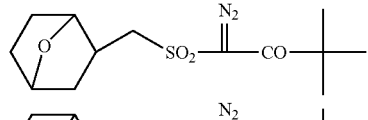
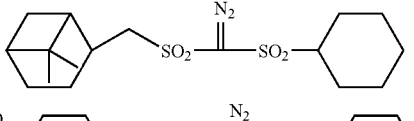

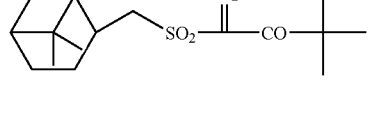
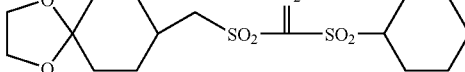

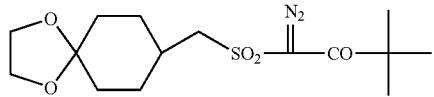
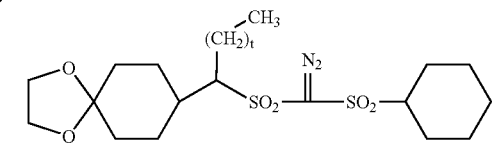

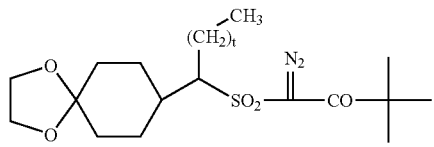
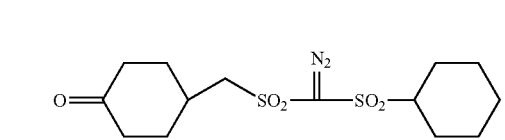

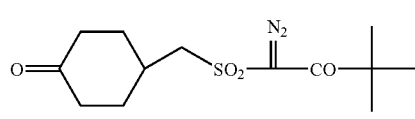
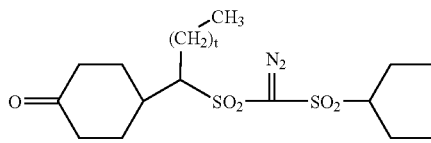

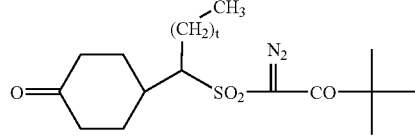

In the above-described formulas, t stands for an integer of from 0 to 5.

The sulfonyldiazomethane compounds represented by formula (1) or formula (1a), (1a') or (1a") are preferably employed as a photoacid generator of a resist material, particularly a chemical amplification resist material, for the fabrication of an integrated circuit sensitive to radiation such as UV rays, deep UV rays, electron beams, X rays, excimer laser, γ rays or synchrotron radiation.

Since the sulfonyldiazomethane compounds represented by formula (1) or formula (1a), (1a') or (1a") have a cyclohexane ring substituted by a sulfonyl group via a methyl group, their crystallinity is lower than that of sulfonyldiazomethane compounds having a cyclic structure substituted directly by a sulfonyl group, whereby the number of insoluble matters remaining upon development and/or removal of a resist film decreases. In addition, owing to an increase in the molecular length and bulkiness, diffusion in the resist film can be suppressed, leading to an improvement of resolution.

The resist material containing the sulfonyldiazomethane of the invention represented by formula (1) or formula (1a), (1a') or (1a") can be used as a positive or negative type. Specific examples of the preferred mode include, but not limited to:

<1> a chemical amplification positive resist material, comprising:

(A) a resin which changes its solubility in an alkali developer by the action of an acid, (B) a sulfonyldiazomethane compound of formula (1) or formula (1a), (1a') or (1a") capable of generating an acid by exposure to radiation, and
(F) an organic solvent;
<2> the chemical amplification positive resist material as described in <1>, further comprising:
(C) a photoacid generator which is capable of generating an acid by exposure to radiation but other than Component (B);
<3> the chemical amplification positive resist material as described in <1> or <2>, further comprising:
(D) a basic additive;
<4> the chemical amplification positive resist material as described in any one of <1> to <3>, further comprising:
(E) an organic acid derivative;
<5> the chemical amplification positive resist material as described in any one of <1> to <4>, further comprising:
(G) a compound which changes its solubility in an alkali developer by the action of an acid and has a molecular weight of 3,000 or less,
<6> a chemical amplification negative resist material, comprising:
(B) the sulfonyldiazomethane compound of formula (1) or formula (1a), (1a') or (1a") capable of generating an acid by exposure to radiation,
(F) an organic solvent,
(H) an alkali soluble resin, and
(I) an acid crosslinking agent for forming a crosslink structure by the action of an acid;
<7> the chemical amplification negative resist material as described in <6>, further comprising (C);
<8> the chemical amplification negative resist material as described in <6> or <7>, further comprising (D); and
<9> the chemical amplification negative resist material as described in any one of <6> to <8>, further comprising:
(J) an alkali soluble compound having a molecular weight of 2500 or less.

A description will next be made of each component in detail.

Although no particular limitation is imposed on the resin (A) which changes its solubility in an alkali developer by the action of an acid, it is an alkali soluble resin having part or all of the phenolic hydroxyl group and/or carboxyl group protected with a acid-labile protecting group having a C—O—C bond.

The above-described alkali-soluble resin having phenolic hydroxyl and/or carboxyl group includes homopolymers and copolymers of p-hydroxystyrene, m-hydroxystyrene, α-methyl-p-hydroxystyrene, 4-hydroxy-2-methylstyrene, 4-hydroxy-3-methylstyrene, hydroxyindene, methacrylic acid and acrylic acid, and copolymers having, at a terminal thereof, a carboxylic derivative or diphenyl ethylene introduced.

Copolymers having, in addition to the above-described unit, another unit free of an alkali soluble site such as styrene, α-methylstyrene, acrylate, methacrylate, hydrogenated hydroxystyrene, maleic anhydride, maleimide, substituted or unsubstituted indene introduced in a proportion not causing a drastic deterioration in the solubility in an alkaline developer can also be used. Substituents for the acrylate or methacrylate may be any one which is not decomposed by an acid. Specific examples include, but not limited to, linear, branched or cyclic $C_{1-8}$ alkyl groups and aromatic groups such as aryl group.

Examples of the alkali-soluble polymers are given below. These polymers may also be used as a raw material for the resin (A) which changes its solubility in an alkaline developer by the action of an acid or as the alkali-soluble resin (H). Examples include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated poly(p-hydroxystyrene) copolymer, poly(p-hydroxystyrene-α-methyl-p-hydroxystyrene) copolymer, poly(p-hydroxystyrene-α-methylstyrene) copolymer, poly(p-hydroxystyrene-styrene) copolymer, poly(p-hydroxystyrene-m-hydroxystyrene) copolymer, poly(p-hydroxystyrene-styrene) copolymer, poly(p-hydroxystyrene-indene) copolymer, poly(p-hydroxystyrene-acrylic acid) copolymer, poly(p-hydroxystyrene-methacrylic acid) copolymer, poly(p-hydroxystyrene-methyl acrylate) copolymer, poly(p-hydroxystyrene-acrylic acid-methyl methacrylate) copolymer, poly(p-hydroxystyrene-methyl methacrylate) copolymer, poly(p-hydroxystyrene-methacrylic acid-methyl methacrylate) copolymer, poly(methacrylic acid), poly(acrylic acid), poly(acrylic acid-methyl acrylate) copolymer, poly(methacrylic acid-methyl methacrylate) copolymer, poly(acrylic acid-maleimide) copolymer, poly(methacrylic acid-maleimide) copolymer, poly(p-hydroxystyrene-acrylic acid-maleimide) copolymer, and poly(p-hydroxystyrene-methacrylic acid-maleimide) copolymer. They may be used singly or in combination of two or more, but are not limited to them.

Preferred are poly(p-hydroxystyrene), partially hydrogenated poly(p-hydroxystyrene) copolymer, poly(p-hydroxystyrene-styrene) copolymer, poly(p-hydroxystyrene-indene) copolymer, poly(p-hydroxystyrene-acrylic acid) copolymer, and poly(p-hydroxystyrene-methacrylic acid) copolymer.

Alkali-soluble resins comprising the following unit (2), (2') or (2") are especially preferred.

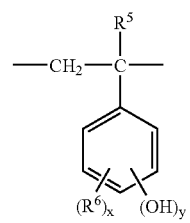

(2)

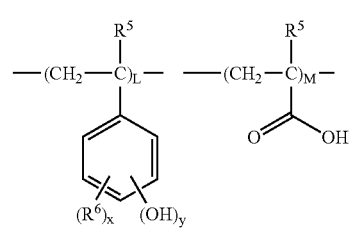

(2')

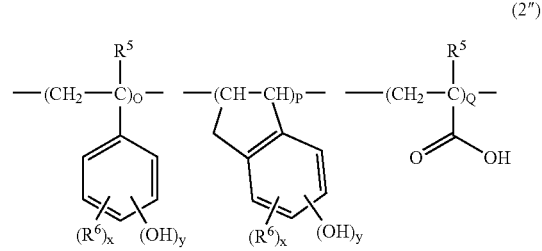

(2")

In the above formula, $R^5$s may be same or different and each represents a hydrogen atom or a methyl group, $R^6$s may be same or different and each represents a linear, branched or cyclic $C_{1-8}$ alkyl group, x stands for 0 or a positive integer and y stands for a positive integer, satisfying x+y≦5, L and M each stands for a positive integer, satisfying O<M/(L+M)≦0.5, and O and P each stands for a positive integer, and Q stands for 0 or a positive integer, satisfying 0<P/(O+P+Q)≦0.5.

The alkali soluble resin having the above-described unit (2) or (2') can be synthesized in a known manner or is commercially available.

The polymer of formula (2") can be synthesized, for example, by carrying out thermal polymerization of an acetoxystyrene monomer, a tertiary alkyl (meth)acrylate monomer and an indene monomer in an organic solvent in the presence of a radical polymerization initiator, subjecting the resulting polymer to alkaline hydrolysis in an organic solvent to deprotect the acetoxy group and obtain a ternary copolymer of hydroxystyrene, tertiary alkyl (meth)acrylate and indene. The term (meth)acrylate as used herein means methacrylate or acrylate.

Examples of the organic solvent used upon polymerization include toluene, benzene, tetrahydrofuran, diethyl ether and dioxane, while those of the polymerization initiator include 2,2'-azobisisobutyronitrile, 2,2'-azobis(2,4-dimethylvaleronitrile), dimethyl-2,2'-azobis(2-methylpropionate), benzoyl peroxide, and lauroyl peroxide. Polymerization is preferably effected by heating at from 50 to 80° C. The reaction time is preferably from about 2 to 100 hours, more preferably from about 5 to 20 hours. For alkaline hydrolysis, bases such as aqueous ammonia and triethylamine may be used. The reaction temperature is preferably from –20 to 100° C., more preferably from 0 to 60° C. The reaction time is preferably from about 0.2 to 100 hours, more preferably from about 0.5 to 20 hours.

Alternatively, the alkali soluble resin may be a polymer having a dendritic or hyperbranched polymer structure as is represented by formula (2'''):

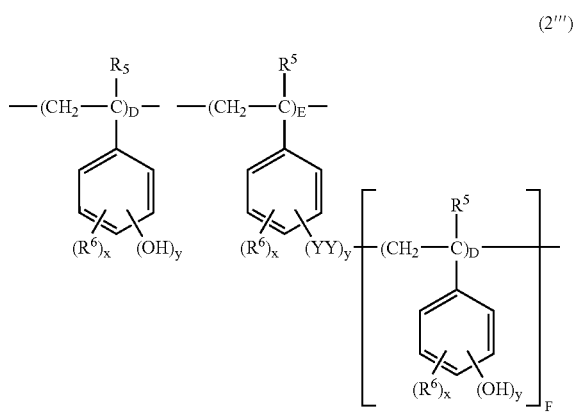

wherein YY represents a divalent organic group selected from $CH_2$, CH(OH), $CR^6$(OH), C=O and $C(OR^6)$(OH) or a trivalent organic group represented by —C(OH)=; Ds may be same or different and each stands for a positive integer and E stands for a positive integer, satisfying E/(D+E)= from 0.001 to 0.1; F stands for 1 or 2; and $R^5$, $R^6$, x and y have the same meanings as described above.

The dendritic or hyperbranched polymer of a phenol derivative can be synthesized by reacting a branching monomer such as chloromethylstyrene as needed upon living anion polymerization of a polymerizable component monomer such as 4-tert-butoxystyrene. They can be synthesized referring to Japanese Patent Application Unexamined Publication No. 2000-344836.

The alkali soluble polymer preferably has a weight-average molecular weight of from 3,000 to 100,000. The compounds having a weight-average molecular weight less than 3,000 may be inferior in the capacity as a polymer, have low heat resistance and have insufficient film forming properties. At weight-average molecular weights exceeding 100,000, on the other hand, problems may occur in solubility in a developer and solubility in a resist solvent owing to excessively large molecular weight. The weight-average molecular weight is determined by gel permeation chromatography (GPC) using polystyrene as a standard.

The molecular weight distribution (Mw/Mn, Mw: weight-average molecular weight, Mn: number-average molecular weight) of the polymer may be 3.5 or less, preferably 1.5 or less. When the molecular weigh distribution exceeds 3.5, deterioration in resolution may occur.

Although no particular limitation is imposed on the preparation process of the compound, a polymer having a low dispersity (narrow dispersion) can be synthesized by employing living anion polymerization for the preparation of poly-p-hydroxystyrene and the like.

It is effective for the resist material of the invention comprising the sulfonyldiazomethane represented by formula (1) to comprise, as the component (A), a resin (particularly, the above-described alkali soluble resin) having a C—O—C bond (acid-labile group) and changing its solubility in an alkali developer by the action of an acid to cut the C—O—C bond. Especially preferred is a polymer having a repeating unit of formula (2), containing phenolic hydroxyl groups, the hydrogen atoms of which have been substituted by one or more acid-labile groups in a proportion greater than 0 mole % but not greater than 80 mole % on the average of the entire hydrogen atoms of the phenolic hydroxyl groups, and having a weight-average molecular weight of from 3,000 to 100,000.

Another preferred polymer is that having a repeating unit of formula (2') (a copolymer comprising p-hydroxystyrene and/or α-methyl-p-hydroxystyrene and acrylic acid and/or methacrylic acid), in which the hydrogen atoms of the carboxyl groups of acrylic acid and/or methacrylic acid have been substituted by one or more acid-labile groups, and the units based on acrylate and methacrylate have been incorporated in a proportion greater than 0 mole % but not greater than 50 mole % on average. In this polymer, part of the phenolic hydroxyl group of p-hydroxystyrene and/or α-methyl-p-hydroxystyrene may be substituted by one or more acid-labile groups. This polymer is preferred when it has the units based on acrylate and/or methacrylate and the units based on p-hydroxystyrene and/or α-methyl-p-hydroxystyrene substituted by an acid-labile group in a proportion greater than 0 mole % but not greater than 80 mole % on average.

More preferred is a polymer having a repeating unit of formula (2") (a copolymer comprising p-hydroxystyrene and/or α-methyl-p-hydroxystyrene, and substituted and/or unsubstituted indene) in which part of the phenolic hydroxyl group of p-hydroxystyrene and/or α-methyl-p-hydroxystyrene have been substituted by one or more acid-labile groups, and part of the carboxyl group of acrylic acid and/or methacrylic acid have been substituted by one or more acid-labile groups. When the substituted indene has a hydroxyl group, part of the hydroxyl group may be substituted with one or more acid-labile groups. In this case, the polymer preferably contains the unit based on p-hydroxystyrene and/or α-methyl-p-hydroxystyrene substituted by an acid-labile group, the unit based on acrylic acid and/or methacrylic acid substituted by an acid-labile group, and the unit based on indene substituted by an acid-labile group in a proportion greater than 0 mole % but not greater than 80 mole % on an average.

The polymer containing a repeating unit represented by the below-described formula (2a), (2a') or (2a") and having a weight-average molecular weight of from 3,000 to 100,000 are preferred.

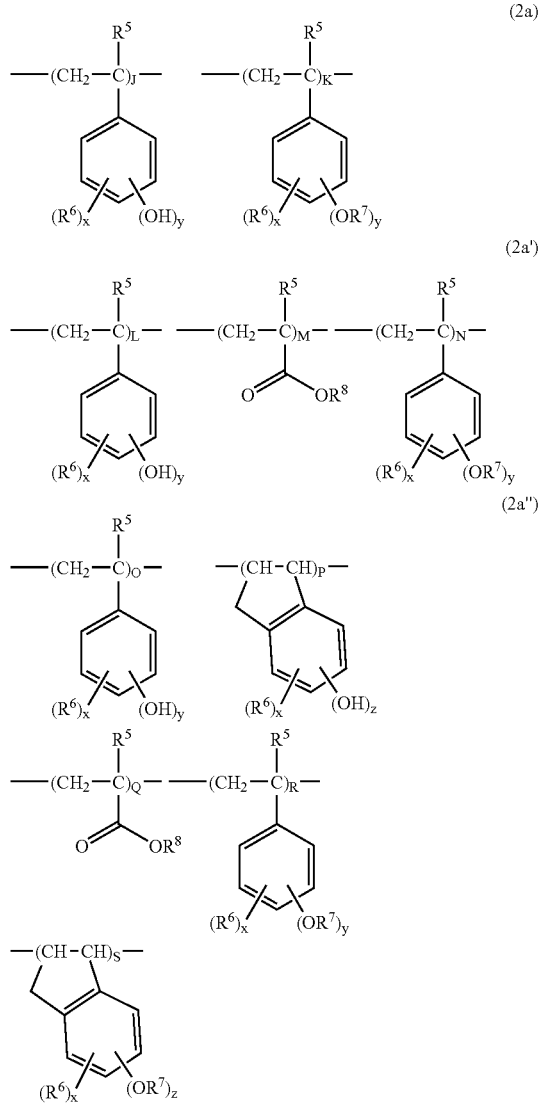

In the above formulas, $R^5$s may be same or different and each represents a hydrogen atom or a methyl group; $R^6$s may be same or different and each represents a linear, branched or cyclic $C_{1-8}$ alkyl group; x stands for 0 or a positive integer and y stands for a positive integer, satisfying $x+y \leq 5$; z stands for 0 or a positive integer satisfying $x+z \leq 4$; $R^7$s may be same or different and each represents an acid-labile group; J and K stand for a positive integer, satisfying $0<K/(J+K) \leq 0.8$; $R^8$s may be same or different and each represents a hydrogen atom or an acid-labile group with the proviso that at least part of $R^8$s represents an acid-labile group; L and M stand for a positive integer, and N stands for 0 or a positive integer, satisfying $0<M/(M+N+L) \leq 0.5$ and $0<(M+N)/(M+N+L) \leq 0.8$; z stands for 0 or a positive integer; and O and P stand for a positive integer, and Q, R and S stand for 0 or a positive integer, satisfying $0<(P+S)/(O+P+Q+R+S) \leq 0.5$ and $0<(Q+R+S)/(O+P+Q+R+S) \leq 0.8$.

$R^6$s may be same or different and each represents a linear, branched or cyclic $C_{1-8}$ alkyl group, for example, methyl, ethyl, propyl, isopropyl, n-butyl, isobutyl, tert-butyl, cyclohexyl or cyclopentyl.

When part of the phenolic hydroxyl group and part or all of the carboxyl group in the alkali soluble resin is protected with an acid-labile substituent represented by a C—O—C bond, a various group is usable as the acid-labile group. In particular, groups of the below-described formulas (4) to (7), tertiary alkyl groups having 4 to 20 carbon atoms, preferably 4 to 15 carbon atoms, a trialkylsilyl group with each alkyl being a $C_{1-6}$ alkyl group, a $C_{4-20}$ oxoalkyl group, and an aryl-substituted $C_{7-20}$ alkyl group are preferred.

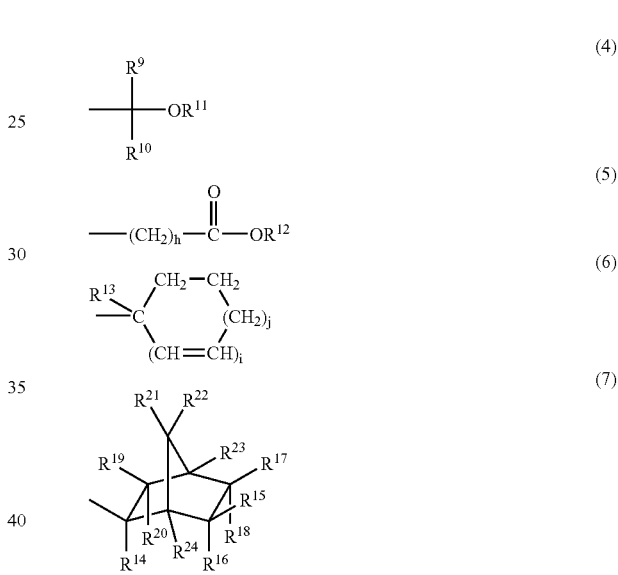

In the above formulas, $R^9$ and $R^{10}$ each represents a hydrogen atom or a linear, branched or cyclic alkyl group having 1 to 18 carbon atoms, preferably 1 to 10 carbon atoms.

Specific examples of $R^9$ or $R^{10}$ include methyl, ethyl, propyl, isopropyl, n-butyl, sec-butyl, tert-butyl, cyclopentyl, cyclohexyl, 2-ethylhexyl and n-octyl.

$R^{11}$ represents a monovalent hydrocarbon group which has 1 to 18 carbon atoms, preferably 1 to 10 carbon atoms, and may have a hetero atom such as an oxygen atom. Examples include linear, branched or cyclic alkyl groups, and these groups having part of hydrogen atoms substituted by a hydroxyl, alkoxy, oxo, amino or alkylamino group. The below-described substituted alkyl groups can be given as specific examples.

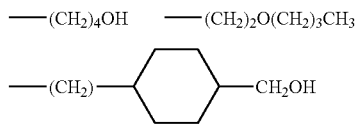

-continued

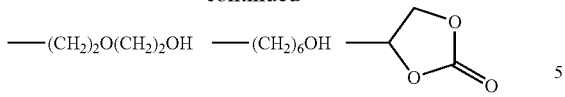

A pair of $R^9$ and $R^{10}$, a pair of $R^9$ and $R^{11}$, or a pair of $R^{10}$ and $R^{11}$ may form a ring. When they form a ring, $R^9$, $R^{10}$ and $R^{11}$ each represents a linear or branched alkylene group having from 1 to 18, preferably from 1 to 10 carbon atoms.

$R^{12}$ represents a tertiary alkyl group having from 4 to 20, preferably 4 to 15 carbon atoms, a trialkylsilyl group having a $C_{1-6}$ alkyl group as each alkyl moiety, a $C_{4-20}$ oxoalkyl group or a group of the above formula (4).

Examples of the tertiary alkyl group as $R^{12}$ include tert-butyl, tert-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl and 1-adamantyl-1-methyl-ethyl. Specific examples of the trialkylsilyl group include trimethylsilyl, triethylsilyl, and dimethyl-tert-butylsilyl. Examples of the oxoalkyl group include 3-oxocyclohexyl, 4-methyl-2-oxooxan-4-yl, and 5-methyl-5-oxooxolan-4-yl. The letter z stands for an integer of from 0 to 6.

$R^{13}$ represents a linear, branched or cyclic $C_{1-8}$ alkyl group or a $C_{6-20}$ aryl group which may be substituted.

Examples of the linear, branched or cyclic alkyl groups include methyl, ethyl, propyl, isopropyl, n-butyl, sec-butyl, tert-butyl, tert-pentyl, n-pentyl, n-hexyl, cyclopentyl, cyclohexyl, cyclopentylmethyl, cyclopentylethyl, cyclohexylmethyl and cyclohexylethyl. Examples of the aryl group which may be substituted include phenyl, methylphenyl, naphthyl, anthryl, phenanthryl and pyrenyl. The letter i stands for 0 or 1, and j stands for 0, 1, 2 or 3, satisfying 2i+j=2 or 3.

$R^{14}$ represents a linear, branched or cyclic $C_{1-8}$ alkyl group or a $C_{6-20}$ aryl group which may be substituted. Examples of it are similar to those described in $R^{13}$.

$R^{15}$ to $R^{24}$ each independently represents a hydrogen atom or a monovalent $C_{1-15}$ hydrocarbon group which may contain a hetero atom. Examples include linear, branched or cyclic alkyl groups such as methyl, ethyl, propyl, isopropyl, n-butyl, sec-butyl, tert-butyl, n-pentyl, tert-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and these groups having part of the hydrogen atoms substituted by hydroxyl, alkoxy, carboxy, alkoxycarbonyl, oxo, amino, alkylamino, cyano, mercapto, alkylthio, or sulfo group.

$R^{15}$ to $R^{24}$ (for example, a pair of $R^{15}$ and $R^{16}$, a pair of $R^{15}$ and $R^{17}$, a pair of $R^{16}$ and $R^{18}$, a pair of $R^{17}$ and $R^{18}$, a pair of $R^{19}$ and $R^{20}$, or a pair of $R^{21}$ to $R^{22}$) may be coupled to form a ring. In this case, these groups each represents a divalent $C_{1-15}$ hydrocarbon group which may contain a hetero atom. Examples include the above-described monovalent hydrocarbon groups from which one hydrogen atom has been eliminated. Any of $R^{15}$ to $R^{24}$ which are bonded to neighboring carbon atoms may be coupled directly to form a double bond (for example, a pair of $R^{15}$ and $R^{17}$, a pair of $R^{17}$ and $R^{23}$, or a pair of $R^{21}$ and $R^{23}$)

Of the acid-labile group of formula (4), specific examples of the linear or branched ones are shown below.

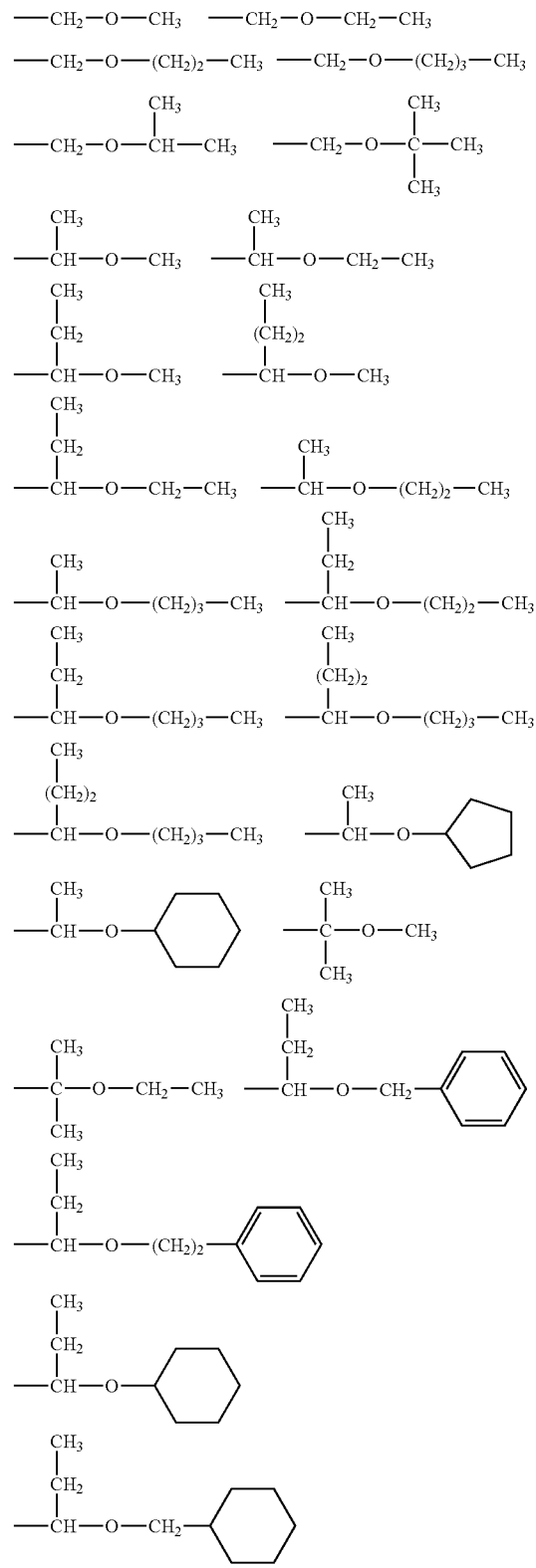

Of the acid-labile group of formula (4), examples of the cyclic groups include tetrahydrofuran-2-yl, 2-methyltetrahydrofuran-2-yl, tetrahydropyran-2-yl and 2-methyltetrahydropyran-2-yl.

Examples of the acid-labile group of formula (5) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxy-carbonylmethyl, 2-tetrahydropyranyloxycarbonylmethyl, and 2-tetrahydrofuranyloxycarbonylmethyl.

Specific examples of the acid-labile group of formula (6) include 1-methylcyclopentyl, 1-ethylcyclopentyl, 1-n-propylcyclopentyl, 1-isopropylcyclopentyl, 1-n-butyl-cyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, 3-ethyl-1-cyclohexen-3-yl, and 1-cyclohexyl-cyclopentyl.

Specific examples of the acid-labile group of formula (7) are given below.

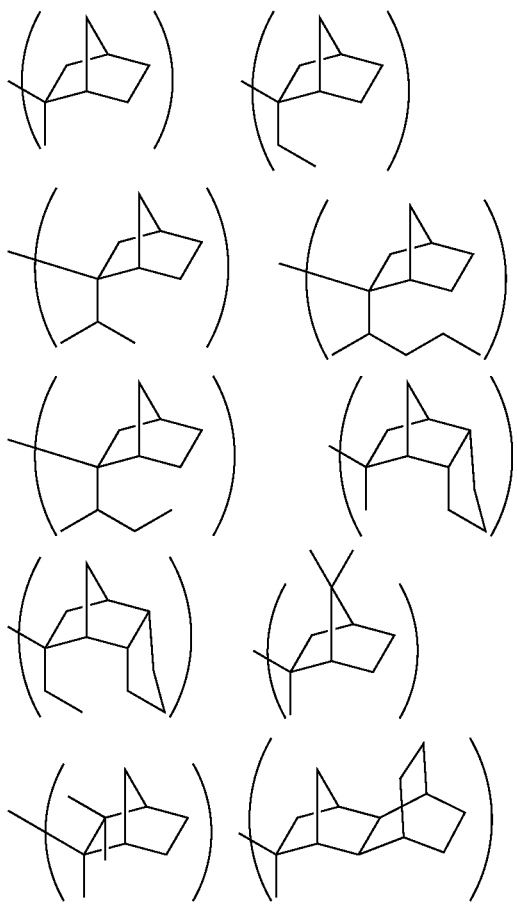

Examples of the tertiary alkyl group having from 4 to 20 carbon atoms, preferably from 4 to 15 carbon atoms include tert-butyl, tert-pentyl, 3-ethyl-3-pentyl and dimethylbenzyl.

Examples of the trialkylsilyl group having a $C_{1-6}$ alkyl group as each alkyl moiety include trimethylsilyl, triethylsilyl and tert-butyldimethylsilyl.

Examples of the $C_{4-20}$ oxoalkyl group include 3-oxocyclohexyl and groups represented by the following formulas.

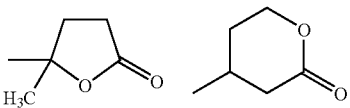

Examples of the aryl-substituted $C_{7-20}$ alkyl groups include benzyl, methylbenzyl, dimethylbenzyl, diphenylmethyl, and 1,1-diphenylethyl.

The resin (A) which is used for the resist material of the invention comprising the sulfonyldiazomethane as a photoacid generator and changes its solubility in an alkaline developer by the action of an acid may be the polymer of formula (2), (2'), (2") or (2''') in which part of the hydrogen atom of the phenolic hydroxyl group have been crosslinked within a molecule and/or between molecules via a C—O—C-containing crosslinking group represented by the below-described formula (8) in a proportion greater than 0 mole % but not greater than 50 mole % on the average of the entire phenolic hydroxyl groups. Concerning specific examples of the polymer crosslinked by an acid-labile group and its synthesis, a reference will be made to Japanese Patent Application Unexamined. Publication No. 11-190904/1999.

(8)

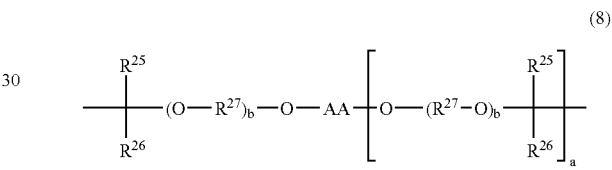

In the above formula, $R^{25}$ and $R^{26}$ each represents a hydrogen atom or a linear, branched or cyclic $C_{1-8}$ alkyl group, or $R^{25}$ and $R^{26}$ may be coupled to form a ring. When they form a ring, $R^{25}$ and $R^{26}$ each represents a linear or branched $C_{1-8}$ alkylene group. $R^{27}$ represents a linear, branched or cyclic $C_{1-10}$ alkylene group. The letter b stands for 0 or an integer of from 1 to 10. The letter AA represents an a-valent aliphatic or alicyclic saturated hydrocarbon group having from 1 to 50 carbon atoms, aromatic hydrocarbon group or heterocyclic group, which group may have a hetero atom therein or in which part of the hydrogen atom attached to the carbon atom may be substituted by a hydroxyl, carboxyl or carbonyl group or a halogen atom.

It is preferred that in formula (8), $R^{25}$ represents a methyl group, $R^{26}$ represents a hydrogen atom, a stands for 1, b stand for 0, and AA stands for ethylene, 1,4-butylene or 1,4-cyclohexylene.

The polymer crosslinked within the molecule and/or between molecules with a C—O—C-containing crosslinking group can be synthesized by reacting a corresponding non-crosslinked polymer with an alkenyl ether in the presence of an acid catalyst in a conventional manner.

If decomposition of the other acid-labile group proceeds under an acid catalyst condition, the intended product can be produced by reacting the alkenyl ether with hydrochloric acid or the like into a halogenated alkyl ether and reacting the resulting compound with the polymer under a basic condition in a conventional manner.

Specific examples of the alkenyl ether include, but not limited to, ethylene glycol divinyl ether, triethylene glycol divinyl ether, 1,2-propanediol divinyl ether, 1,3-propanediol divinyl ether, 1,3-butanediol divinyl ether, 1,4-butanediol divinyl ether, neopentyl glycol divinyl ether, trimethylolpropane trivinyl ether, trimethylolethane trivinyl ether, hexanediol divinyl ether, and 1,4-cyclohexanediol divinyl ether.

In the chemical amplification positive resist material of the invention, the resin used as component (A) is as described above. Examples of the preferred acid-labile group for a phenolic hydroxyl group include 1-ethoxyethyl, 1-ethoxypropyl, tetrahydrofuranyl, tetrahydropyranyl, tert-butyl, tert-pentyl, 1-ethylcyclohexyloxycarbonylmethyl, tert-butoxycarbonyl, tert-butoxycarbonylmethyl, and substituents of formula (8) wherein $R^{25}$ is methyl, $R^{26}$ is hydrogen, a is 1, b is 0, and AA is ethylene, 1,4-butylene or 1,4-cyclohexylene. The hydrogen atoms of carboxyl groups of methacrylic acid or acrylic acid are preferably protected with a substituent such as tert-butyl, tert-pentyl, 2-methyl-2-adamantyl, 2-ethyl-2-adamantyl, 1-ethylcyclopentyl, 1-ethylcyclohexyl, 1-cyclohexylcyclopentyl, 1-ethylnorbornyl, tetrahydrofuranyl or tetrahydropyranyl.

The number of the substituents in one polymer may be either one or two or more. A blend of two or more polymers having different substituents can also be used.

Although a ratio of these substituents for phenol or carboxyl groups in the polymer is not limited, it is adjusted so that a dissolution rate of the unexposed area upon application of the resist composition onto a substrate falls within a range of from 0.01 to 10 Å/sec (angstrom/sec) (when a 2.38 wt % TMAH (tetramethylammonium hydroxide) developer is used).

When the polymer has a high carboxyl content, it is necessary to lower the alkali dissolution rate by increasing the substitution ratio or introducing a non-acid-decomposable substituent which will be described later.

When the acid-labile group for crosslinking in the molecule and/or within the molecules are to be introduced, a ratio of the substituents introduced by crosslinking is preferably adjusted to 20 mole % or less, preferably 10 mole % or less on an average based on the entire hydrogen atom of the phenolic hydroxyl group of the polymer. If the substituent ratio exceeds the above-described range, an increase in the molecular weight due to crosslinking may lead to deterioration in dissolution, stability and resolution. It is more preferred to introduce another non-crosslinking acid-labile group into the crosslinked polymer at a substituent ratio not greater than 10 mole % on average to adjust the dissolution rate to fall within the above range.

When poly(p-hydroxystyrene) is used, the optimum substituent ratio differs between a substituent having a strong dissolution inhibitory action such as a tert-butoxycarbonyl group and a substituent having a weak dissolution inhibitory action such as an acetal group, but the total substituent ratio is preferably adjusted to from 10 to 40 mole %, more preferably from 20 to 30 mole % on average based on the entire hydrogen atoms of phenolic hydroxyl groups of the polymer.

Polymers having such an acid-labile group introduced therein have preferably a weight-average molecular weight of from 3,000 to 100,000. The polymers having a weight-average molecular weight less than 3000 may be inferior in the capacity as a polymer and may have lower heat resistance and insufficient film forming property. The polymers having the molecular weight greater than 100,000, on the other hand, may have problems in solubility in a developer or solubility in a resist solvent owing to excessively large molecular weight.

When a non-crosslinking acid-labile group is used, the polymer preferably has a dispersity not greater than 3.5, preferably not greater than 1.5. The dispersity greater than 3.5 often results in deterioration of resolution. When a crosslinking acid-labile group is used, the alkali soluble resin serving as a raw material preferably has a dispersity not greater than 1.5. The dispersity preferably does not exceed 3 even after protection with a crosslinking type acid-labile group. When the dispersity is greater than 3, lowering in dissolution, application properties, storage stability and resolution tends to occur.

In order to impart various functions to the resist material, a substituent may be introduced into part of the phenolic hydroxyl group or carboxyl group of the polymer protected by the acid-labile group. The substituent is, for example, a substituent for improving adhesion with a substrate, a non-acid-decomposable group for adjusting the solubility in an alkali developer and a substituent for improving etching resistance. Examples include, but not limited to, 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxoranyl, 4-methyl-2-oxo-4-oxanyl, methyl, ethyl, propyl, n-butyl, sec-butyl, acetyl, pivaloyl, adamantyl, isoboronyl, and cyclohexyl.

Although the amount of the resin as Component (A) added to the resist material of the invention is not limited, it is preferably from 65 to 99 parts by weight, more preferably from 65 to 98 parts by weight per 100 parts by weight of the solid content in the resist material. The term "solid content" as used herein means all the components of the resist material of the invention except the solvent.

Specific examples of the sulfonyldiazomethane represented by formula (1), (1a), (1a') or (1a") to be used as Component (B) are as described above.

The addition amount of the sulfonyldiazomethane represented by formula (1), (1a), (1a') or (1a") to the chemical amplification resist material may be 10 parts by weight or less, preferably from 1 to 5 parts by weight per 100 parts by weight of the solid content in the resist material. When the amount is less than the above-described range, an amount of the acid enough for deprotecting the acid-labile group in the polymer cannot always be generated. When the amount exceeds the above-described range, on the other hand, the transmittance of the resist film may lower excessively, failing to form a rectangular pattern, and presumably causing problems such as abnormality of particles and deposits during storage of the resist material. The photoacid generator as Component (B) may be used singly or in combination of two or more.

When an acid generator other than the sulfonyldiazomethane of the invention represented by formula (1), (1a), (1a') or (1a") is added as a photoacid generator (C), any compound capable of generating an acid upon exposure to high energy radiation such as UV rays, deep UV rays, electron beams, X rays, excimer laser, γ rays or synchrotron radiation can be used.

Preferred examples of the photoacid generator include sulfonium salts, iodonium salts, sulfonyldiazomethane and N-sulfonyloxydicarboxyimide photoacid generators. Examples of it will next be described more specifically. They may be used singly or in combination of two or more.

Sulfonium salts are salts of a sulfonium cation with a sulfonate. Examples of the sulfonium cation include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)-phenylsulfonium, tris(4-methylphenyl)sulfonium, tris(4-tert-butylphenyl)sulfonium, tris(phenylmethyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium and 2-oxo-2-phenylethylthiacyclopentanium. Examples of the sulfonate include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, bis(trifluoromethanesulfonyl)imide, bis(perfluoroethanesulfonyl)imide, bis(perfluorobutanesulfonyl)imide, tris(trifluoromethanesulfonyl)methide and tris(perfluoroethanesulfonyl)methide. Sulfonium salts are combinations of the above-described sulfonium cation and sulfonate.

Iodinium salts are salts of an iodonium cation with a sulfonate. Examples of the iodinium cation include aryliodonium cations such as diphenyliodinium, bis(4-tert-butylphenyl)iodonium, 4-tert-butoxyphenylphenyliodonium, and 4-methoxyphenylphenyliodonium. Examples of the sulfonate include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, bis(trifluoromethanesulfonyl)imide, bis(perfluoroethanesulfonyl)imide, bis(perfluorobutanesulfonyl)imide, tris(trifluoromethanesulfonyl)methide and tris(perfluoroethanesulfonyl)methide. Iodonium salts are the combinations of the above-described iodonium cation and sulfonate.

Examples of the sulfonyldiazomethane include bissulfonyldiazomethanes and sulfonylcarbonyldiazomethanes such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(4-acetyloxyphenylsulfonyl)diazomethane, bis(4-methanesulfonyloxyphenylsulfonyl)diazomethane, bis(4-(p-toluenesulfonyloxy)phenylsulfonyl)diazomethane, bis(2-naphthylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

A N-sulfonyloxydicarboxyimide photoacid generator may be a combination of an imide skeleton and a sulfonate. Examples of the imide skeleton include succinimide, naphthalene dicarboxyimide, phthalimide, cyclohexyldicarboxyimide, 5-norbornene-2,3-dicarboxyimide, and 7-oxabicyclo [2.2.1]-5-heptene-2,3-dicarboxyimide. Examples of the sulfonate include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, and methanesulfonate.

A benzoinsulfonate photoacid generator includes benzoin tosylate, benzoin mesylate, and benzoin butanesulfonate.

A pyrogallol trisulfonate photoacid generator includes pyrogallol, fluoroglycine, catechol, resorcinol, hydroquinone, in which all the hydroxyl groups have been substituted with trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate.

A nitrobenzyl sulfonate photoacid generator includes 2,4-dinitrobenzyl sulfonate, 2-nitrobenzyl sulfonate, and 2,6-dinitrobenzyl sulfonate. Specific examples of the sulfonate include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate. Compounds having a benzyl-side nitro group substituted with a trifluoromethyl group can also be used similarly.

Examples of the sulfone photoacid generator include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-(cyclohexylcarbonyl)-2-(p-toluenesulfonyl)propane, and 2,4-dimethyl-2-(p-toluenesulfonyl)pentan-2-one.

Example of the glyoxime derivative type photoacid generator include compounds as described in Japanese Patent No. 2906999 and Japanese Patent Application Unexamined Publication No. 9-301948/1997. Specific examples include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-trifluoromethylbenzenesulfonyl)-α-dimethylglyoxime, bis-O-(xylenesulfonyl)-α-dimethylglyoxime, bis-O-(trifluoromethanesulfonyl)nioxime, bis-O-(2,2,2-trifluoroethanesulfonyl)nioxime, bis-O-(10-camphorsulfonyl)nioxime, bis-O-(benzenesulfonyl)nioxime, bis-O-(p-fluorobenzenesulfonyl)nioxime, bis-O-(p-trifluoromethylbenzenesulfonyl)nioxime, and bis-O-(xylenesulfonyl)nioxime.

Additional examples include the oxime sulfonates as described in U.S. Pat. No. 6,004,724, particularly, (5-(p-toluenesulfonyl)oxyimino-5H-thiophen-2-ylidene)phenylacetonitrile, (5-(10-camphorsulfonyl)oxyimino-5H-thiophen-2-ylidene)phenyl-acetonitrile, (5-(n-octanesulfonyl)oxyimino-5H-thiophen-2-ylidene)phenylacetonitrile, (5-(p-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, and (5-n-octanesulfonyloxyimino-5H-thiophen-2-ylidene)(2-methylphenyl)acetonitrile.

Further additional examples include the oxime sulfonate as described in U.S. Pat. No. 6,261,738 and Japanese Patent Application Unexamined Publication No. 2000-314956, particularly, 2,2,2-trifluoro-1-phenyl-ethanone oxime-O-methylsulfonate, 2,2,2-trifluoro-1-phenyl-ethanone oxime-O-(10-camphorylsulfonate), 2,2,2-trifluoro-1-phenyl-ethanone oxime-O-(4-methoxyphenylsulfonate), 2,2,2-trifluoro-1-phenyl-ethanone oxime-O-(1-naphthylsulfonate), 2,2,2-trifluoro-1-phenyl-ethanone oxime-O-(2-naphthylsulfonate), 2,2,2-trifluoro-1-phenyl-ethanone oxime-O-(2,4,6-trimethylphenylsulfonate), 2,2,2-trifluoro-1-(4-methylphenyl)-ethanone oxime-O-(10-camphorylsulfonate), 2,2,2-trifluoro-1-(4-methylphenyl)-ethanone oxime-O-(methylsulfonate), 2,2,2-trifluoro-1-(2-methylphenyl)-ethanone oxime-O-(10-camphorylsulfonate), 2,2,2-trifluoro-1-(2,4-dimethylphenyl)-ethanone oxime-O-(10-camphorylsulfonate), 2,2,2-trifluoro-1-(2,4-dimethylphenyl)-ethanone oxime-O-(1-naphthylsulfonate), 2,2,2-trifluoro-1-(2,4-dimethylphenyl)-ethanone oxime-O-(2-naphthylsulfonate), 2,2,2-trifluoro-1-(2,4,6-trimethylphenyl)-ethanone oxime-O-(10-camphorylsulfonate), 2,2,2-trifluoro-1-(2,4,6-trimethylphenyl)-ethanone oxime-O-(1-naphthylsulfonate), 2,2,2-trifluoro-1-(2,4,6-trimethylphenyl)-ethanone oxime-O-(2-naphthylsulfonate), 2,2,2-trifluoro-1-(4-methoxyphenyl)-ethanone oxime-O-methylsulfonate, 2,2,2-trifluoro-1-(4-methylthiophenyl)-ethanone oxime-O-methylsulfonate, 2,2,2-trifluoro-1-(3,4-dimethoxyphenyl)-ethanone oxime-O-methylsulfonate, 2,2,3,3,4,4,4-heptafluoro-1-phenyl-butanone oxime-O-(10-camphorylsulfonate), 2,2,2-trifluoro-1-(phenyl)-ethanone oxime-O-methylsulfonate, 2,2,2-trifluoro-1-(phenyl)-ethanone oxime-O-10-camphorylsulfonate, 2,2,2-trifluoro-1-(phenyl)-ethanone oxime-O-(4-methoxyphenyl)sulfonate, 2,2,2-trifluoro-1-(phenyl)-ethanone oxime-O-(1-naphthyl)-sulfonate, 2,2,2-trifluoro-1-(phenyl)-ethanone oxime-O-(2-naphthyl)sulfonate, 2,2,2-trifluoro-1-(phenyl)-ethanone oxime-O-(2,4,6-trimethylphenyl)sulfonate, 2,2,2-trifluoro-1-(4-methylphenyl)-ethanone oxime-O-(10-camphoryl) sulfonate, 2,2,2-trifluoro-1-(4-methylphenyl)-ethanone oxime-O-methylsulfonate, 2,2,2-trifluoro-1-(2-methylphenyl)-ethanone oxime-O-(10-camphoryl)sulfonate, 2,2,2-trifluoro-1-(2,4-dimethylphenyl)-ethanone oxime-O-(1-naphthyl)sulfonate, 2,2,2-trifluoro-1-(2,4-dimethylphenyl)-ethanone oxime-O-(2-naphthyl)sulfonate, 2,2,2-trifluoro-1-(2,4,6-trimethylphenyl)-ethanone oxime-O-(10-camphoryl)sulfonate, 2,2,2-trifluoro-1-(2,4,6-trimethylphenyl)-ethanone oxime-O-(1-naphthyl)sulfonate, 2,2,2-trifluoro-1-(2,4,6-trimethylphenyl)-ethanone oxime-O-(2-naphthyl)sulfonate, 2,2,2-trifluoro-1-(4-methoxyphenyl)-ethanone oxime-O-methylsulfonate, 2,2,2-trifluoro-1-(4-thiomethylphenyl)-ethanone oxime-O-methylsulfonate, 2,2,2-trifluoro-1-(3,4-dimethoxyphenyl)-ethanone oxime-O-methylsulfonate, 2,2,2-trifluoro-1-(4-methoxyphenyl)-ethanone oxime-O-(4-methylphenyl)sulfonate, 2,2,2-trifluoro-1-(4-methoxyphenyl)-ethanone oxime-O-(4-methoxyphenyl)sulfonate, 2,2,2-trifluoro-1-(4-methoxyphenyl)-ethanone oxime-O-(4-dodecylphenyl)sulfonate, 2,2,2-trifluoro-1-(4-methoxyphenyl)-ethanone oxime-O-octylsulfonate, 2,2,2-trifluoro-1-(4-thiomethylphenyl)-ethanone oxime-O-(4-methoxyphenyl)sulfonate, 2,2,2-trifluoro-1-(4-thiomethylphenyl)-ethanone oxime-O-(4-dodecylphenyl)sulfonate, 2,2,2-trifluoro-1-(4-thiomethylphenyl)-ethanone oxime-O-octylsulfonate, 2,2,2-trifluoro-1-(4-thiomethylphenyl)-ethanone oxime-O-(2-naphthyl)sulfonate, 2,2,2-trifluoro-1-(2-methylphenyl)-ethanone oxime-O-methylsulfonate, 2,2,2-trifluoro-1-(4-methylphenyl)ethanone oxime-O-phenylsulfonate, 2,2,2-trifluoro-1-(4-chlorophenyl)-ethanone oxime-O-phenylsulfonate, 2,2,3,3,4,4,4-heptafluoro-1-(phenyl)-butanone oxime-O-(10-camphoryl)sulfonate, 2,2,2-trifluoro-1-naphthyl-ethanone oxime-O-methylsulfonate, 2,2,2-trifluoro-2-naphthyl-ethanone oxime-O-methylsulfonate, 2,2,2-trifluoro-1-[4-benzylphenyl]-ethanone oxime-O-methylsulfonate, 2,2,2-trifluoro-1-[4-(phenyl-1,4-dioxa-but-1-yl)phenyl]-ethanone oxime-O-methylsulfonate, 2,2,2-trifluoro-1-naphthyl-ethanone oxime-O-propylsulfonate, 2,2,2-trifluoro-2-naphthyl-ethanone oxime-O-propylsulfonate, 2,2,2-trifluoro-1-[4-benzylphenyl]-ethanone oxime-O-propyl-sulfonate, 2,2,2-trifluoro-1-[4-methylsulfonylphenyl]-ethanone oxime-O-propylsulfonate, 1,3-bis[1-(4-phenoxyphenyl)-2,2,2-trifluoroethanone oxime-O-sulfonyl]phenyl, 2,2,2-trifluoro-1-[4-methylsulfonyloxyphenyl]-ethanone oxime-O-propylsulfonate, 2,2,2-trifuoro-1-[4-methylcarbonyloxyphenyl]-ethanone oxime-O-propylsulfonate, 2,2,2-trifluoro-1-[6H,7H-5,8-dioxonaphth-2-yl)-ethanone oxime-O-propylsulfonate, 2,2,2-trifluoro-1-[4-methoxycarbonylmethoxyphenyl]-ethanone oxime-O-propylsulfonate, 2,2,2-trifluoro-1-[4-(methoxycarbonyl)-(4-amino-1-oxa-pent-1-yl)-phenyl]-ethanone oxime-O-propylsulfonate, 2,2,2-trifluoro-1-[3,5-dimethyl-4-ethoxyphenyl)-ethanone oxime-O-propylsulfonate, 2,2,2-trifluoro-1-[4-benzyloxyphenyl]-ethanone oxime-O-propylsulfonate, 2,2,2-trifluoro-1-[2-thiophenyl]-ethanone oxime-O-propylsulfonate, and 2,2,2-trifluoro-1-[1-dioxathiophen-2-yl]-ethanone oxime-O-propylsulfonate.

Further additional examples include oxime sulfonates as described in Japanese Patent Application Unexamined Publications Nos. 9-95479 and 9-230588/1997, and those described therein as the background art, for example, α-(p-toluenesulfonyloxyimino)phenylacetonitrile, α-(p-chlorobenzenesulfonyloxyimino)phenylacetonitrile, α-(4-nitrobenzenesulfonyloxyimino)phenylacetonitrile, α-(4-nitro-2-trifluoromethylbenzenesulfonyloxyimino)

phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylacetonitrile, α-(benzenesulfonyloxyimino)-2-thienylacetonitrile, α-(4-dodecylbenzenesulfonyloxyimino)phenylacetonitrile, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Examples of the bisoxime sulfonate include compounds as described in Japanese Patent Application Unexamined Publication No. 9-208554/1997, particularly, bis(α-(p-toluenesulfonyloxy)imino)-p-phenylenediacetonitrile, bis(α-(benzenesulfonyloxy)imino]-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(p-toluenesulfonyloxy)imino)-p-phenylenediacetonitrile, bis(α-(trifluoromethanesulfonyloxy)imino)-p-phenylenediacetonitrile, bis(α-(4-methoxybenzenesulfonyloxy)imino)-p-phenylenediacetonitrile, bis(α-(p-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(4-toluenesulfonyloxy)imino)-m-phenylenediacetonitrile, bis(α-(trifluoromethanesulfonyloxy)imino)-m-phenylenediacetonitrile, and bis(α-(4-methoxybenzenesulfonyloxy)imino)-m-phenylenediacetonitrile.

Of these, sulfonium salts, bissulfonyldiazomethanes, N-sulfonyloxyoxyimides and glyoxime derivatives are preferably employed as a photoacid generator, with sulfonium salts, bissulfonyldiazomethanes and N-sulfonyloxyimides being more preferred. Specific examples include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(p-toluenesulfonyloxy)benzenesulfonate, triphenylsulfonium 2,4,6-triisopropylbenzenesulfonate, 4-tert-butyoxyphenyldiphenylsulfonium, p-toluenesulfonate, 4-tert-butoxyphenyldiphenylsulfonium camphorsulfonate, 4-tert-butoxyphenyldiphenylsulfonium 4-(p-toluenesulfonyloxy)benzenesulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenylsulfonyl)diazomethane, bis(4-tert-butylphenylsulfonyl)diazomethane, N-camphorsulfonyloxy-5-norbornene-2,3-carboximide, and N-p-toluenesulfonyloxy-5-norbornene-2,3-carboximide.

Although the amount of the photoacid generator (C), which is other than the sulfonyldiazomethane represented by formula (1), (1a), (1a') or (1a") and is added to the chemical amplification resist material of the invention is not particular limited insofar as it does not impair the effects of the invention, it is preferably from 0 to 10 parts by weight, more preferably from 0 to 5 parts by weight per 100 parts by weight of the solid content in the resist material. Excessively large amounts may cause deterioration in resolution or a problem of foreign matters upon development/resist peeling. The above-described photoacid generator (C) may be used singly or in combination of two or more. The transmittance of the resist film can be controlled by using a photoacid generator having a low transmittance at the exposure wavelength and adjusting its amount upon addition.

The resist material of the invention may further contain a compound which is decomposed to generate an acid by the action of an acid. Such a compound is called "acid proliferating compound" and described in J. Photopolym. Sci. and Tech., 8, 43-44, 45-46(1995), and J. Photopolym. Sci. and Tech., 9, 29-30(1996).

Examples of the acid proliferating compound include, but not limited to, tert-butyl-2-methyl-2-tosyloxymethyl acetoacetate and 2-phenyl-2-(2-tosyloxyethyl)-1,3-dioxolane. Of the known photoacid generators, compounds poor in stability, particularly in thermal stability, tend to behave like the acid proliferating compound.

The amount of the acid proliferating compound to be added to the resist material of the invention comprising the sulfonyldiazomethane as a photoacid generator is preferably 2 parts by weight or less, more preferably 1 part by weight or less per 100 parts by weight of the solid content in the resist material. Excessive addition of it may make diffusion control difficult, tending to cause deterioration in resolution and pattern shape.

As the basic compound serving as component (D), a compound capable of suppressing a diffusion rate of an acid generated by a photoacid generator in a resist film is suited. By incorporating such a basic compound, the diffusion rate of an acid in a resist film can be suppressed, leading to an improvement in resolution. In addition, it can suppress a change in sensitivity after exposure and reduce dependence on the substrate or environment, and thereby can improve the exposure latitude and the pattern profile.

Examples of such a basic compound include primary, secondary, and tertiary aliphatic amines, mixed amines, aromatic amines, heterocyclic amines, carboxy-containing nitrogenous compounds, sulfonyl-containing nitrogenous compounds, hydroxyl-containing nitrogenous compounds, hydroxyphenyl-containing nitrogenous compounds, alcoholic nitrogenous compounds, amide derivatives, and imide derivatives.

Specific examples of the primary aliphatic amines include ammonia, methylamine, ethylamine, n-propylamine, isopropylamine, n-butylamine, isobutylamine, sec-butylamine, tert-butylamine, n-pentylamine, tert-pentylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Specific examples of the secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine.

Specific examples of the tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include dimethylethylamine, methylethylpropylamine, benzylamine, phenethylamine, and benzyldimethylamine.

Specific examples of the aromatic amines and heterocyclic amines include aniline derivatives (such as aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (such as pyrrole, 2H-pyrrole, 1-methylpyrrole, 2,4-dimethylpyrrole, 2,5-dimethylpyrrole, and N-methylpyrrole), oxazole derivatives (such as oxazole and isooxazole), thiazole derivatives (such as thiazole and isothiazole), imidazole derivatives (such as imidazole, 4-methylimidazole, and 4-methyl-2-phenylimidazole), pyrazole derivatives, furazan derivatives, pyrroline derivatives (such as pyrroline and 2-methyl-1-pyrroline), pyrrolidine derivatives (such as pyrrolidine, N-methylpyrrolidine, pyrrolidinone, and N-methylpyrrolidone), imidazoline derivatives, imidazolidine derivatives, pyridine derivatives (such as pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (such as quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Specific examples of the carboxy-containing nitrogenous compounds include aminobenzoic acid, indolecarboxylic acid, and amino acid derivatives (such as nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of the sulfonyl-containing nitrogenous compounds include 3-pyridinesulfonic acid and pyridinium p-toluenesulfonate.

Examples of the hydroxy-containing nitrogenous compounds, hydroxyphenyl-containing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of the amide derivatives include formamide, N-methylformamide, N,N-dimethylformamide, acetamide, N-methylacetamide, N,N-dimethylacetamide, propionamide, and benzamide.

Examples of the imide derivatives include phthalimide, succinimide, and maleimide.

It is also possible to add one or more basic compounds selected from the compounds represented by formula (A1):

$$N(X')_w(Y)_{3-w} \qquad (A1)$$

wherein w stands for 1, 2 or 3, Ys each independently represents a hydrogen atom or a linear, branched or cyclic $C_{1-20}$ alkyl group which may contain a hydroxyl group or ether structure, and X's each independently represents a group represented by formula (X'1), (X'2) or (X'3), or two or three X's may be coupled to form a ring.

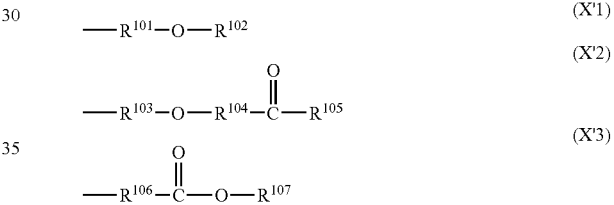

Herein $R^{101}$, $R^{103}$ and $R^{106}$ each represents a linear or branched $C_{1-4}$ alkylene group, $R^{102}$, $R^{105}$ and $R^{107}$ each represents a hydrogen atom or a linear, branched or cyclic $C_{1-20}$ alkyl group which may contain at least one hydroxyl group, ether structure, ester structure or lactone ring, and $R^{104}$ represents a single bond or a linear or branched $C_{1-4}$ alkylene group.

Specific examples of the basic compound of formula (A1) include tris(2-methoxymethoxyethyl)amine, tris[2-(2-methoxyethoxy)ethyl]amine, tris[2-(2-methoxyethoxymethoxy)ethyl]amine, tris[2-(1-methoxyethoxy)ethyl]amine, tris[2-(1-ethoxyethoxy)ethyl]amine, tris[2-(1-ethoxypropoxy)ethyl]amine, tris{2-[2-(2-hydroxyethoxy)ethoxy]ethyl}amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxy-carbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, and β-(diethylamino)-δ-valerolactone.

It is also possible to incorporate one or more compounds selected from the basic compounds having a cyclic structure represented by formula (A2):

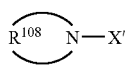

(A2)

wherein X' has the same meaning as described above, and $R^{108}$ represents a linear or branched $C_{2-20}$ alkylene group which may contain at least one carbonyl group, ether structure, ester structure or sulfide structure.

Specific examples of the basic compound having a cyclic structure represented by formula (A2) include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)-propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)-propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

It is also possible to incorporate one or more compounds selected from the cyano-containing basic compounds represented by formulas (A3) to (A6):

(A3)

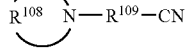

(A4)

(A5)

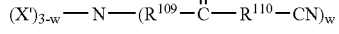

(A6)

wherein X', $R^{108}$ and w have the same meanings as described above, and $R^{109}$ and $R^{110}$ each independently represents a linear or branched $C_{1-4}$ alkylene group.

Specific examples of the cyano-containing basic compounds represented by the formulas (A3) to (A6) include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-(cyanomethyl)-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The above-described basic compounds may be used singly or in combination of two or more. The basic compound is added preferably in an amount of from 0 to 2 parts by weight, especially preferably from 0.01 to 1 part by weight per 100 parts by weight of the solid content in the resist material. Amounts exceeding 2 parts by weight may cause excessive lowering in the sensitivity.

Although no particular limitation is imposed on the examples of the organic acid derivative as Component (E), specific examples include phenol, cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used singly or in combination of two or more.

The organic acid derivative may be added to the chemically amplified resist material of the invention preferably in an amount not greater than 5 parts by weight, more preferably 1 part by weight or less per 100 parts by weight of the solid content in the resist material. Amounts exceeding 5 parts by weight may deteriorate resolution. The addition of this organic acid derivative is not essential, depending on the combination of the components of the resist material.

Examples of the organic solvent as Component (F) include, but not limited to, butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methyl pyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethyl sulfoxide, γ-butyrolactone, propylene glycol methyl ether acetate, propylene glycol ethyl ether acetate, propylene. glycol propyl ether acetate, methyl lactate, ethyl lactate, propyl lactate, and tetramethylenesulfone. Of these, propylene glycol alkyl ether acetate and alkyl lactate are especially preferred.

These solvents may be used singly or as a mixture of two or more.

A preferred example of a mixed solvent is a mixture of propylene glycol alkyl ether acetate and alkyl lactate.

The propylene glycol alkyl ether acetate in the invention has a $C_{1-4}$ alkyl group, for example, methyl, ethyl or propyl, with methyl or ethyl being especially preferred. The propylene glycol alkyl ether acetate includes 1,2- and 1,3-substituted ones and each has three isomers depending on the combination of substitution positions. They may be used singly or as a mixture.

When the propylene glycol alkyl ether acetate is used as the solvent, it is added preferably in an amount of 50 wt % or greater based on the entire solvent. When the alkyl lactate is used as the solvent, it is added preferably in an amount of 50 wt % or greater based on the entire solvent. When a mixture of the propylene glycol alkyl ether acetate and alkyl lactate is used as the solvent, the mixture is preferably added in a total amount of 50 wt % or greater based on the entire solvent. In this case, the mixture preferably comprises 60 to 95 wt % of the propylene glycol alkyl ether acetate and from 5 to 40 wt % of the alkyl lactate. A too small proportion of the propylene glycol alkyl ether acetate may lead to deterioration in application properties, while a too large proportion of it may lead to problems of insufficient dissolution, particles and generation of foreign matters. On the other hand, a too small proportion of the alkyl lactate may cause problems of insufficient dissolution, particles and generation of foreign matters, while a too large proportion of it may lead to deterioration in storage stability, as well as deterioration in application properties due to an increased viscosity.

The solvent may be added preferably in an amount of from 300 to 2,000 parts by weight, more preferably from 400 to 1,000 parts by weight per 100 parts by weight of the solid content of the chemical amplification resist material. The concentration of the solvent is however not limited thereto insofar it permits film formation by any one of the existing processes.

As a compound (dissolution inhibitor) (G) having a molecular weight not greater than 3000 and changing its solubility in an alkali developer by the action of an acid, a compound obtained by partially or entirely substituting a phenol or carboxylic acid derivative having a molecular weight as low as 2500 or less with an acid-labile substituent may be added.

Examples of the phenol or carboxylic acid derivative having a weight-average molecular weight not greater than 2500 include bisphenol A, bisphenol H, bisphenol S, 4,4-bis(4'-hydroxyphenyl)valeric acid, tris(4-hydroxyphenyl) methane, 1,1,1-tris(4'-hydroxyphenyl)ethane, 1,1,2-tris(4'-hydroxyphenyl)ethane, phenolphthalein, and thymolphthalein. As the acid-labile substituent, those described above as the acid-labile groups of the polymer can be given as examples.

Preferred examples of the dissolution inhibitor include bis(4-(2''-tetrahydropyranyloxy)phenyl)methane, bis(4-(2''-tetrahydrofuranyloxy)phenyl)methane, bis(4-tert-butoxyphenyl)methane, bis(4-tert-butoxycarbonyloxyphenyl) methane, bis(4-tert-butoxycarbonylmethyloxyphenyl) methane, bis[4-(1'-ethoxyethoxy)phenyl]methane, bis[4-(1'-ethoxypropyloxy)phenyl]methane, 2,2-bis[4'-(2''-tetrahydropyranyloxy)]propane, 2,2-bis[4'-(2''-tetrahydrofuranyloxy)phenyl]propane, 2,2-bis(4'-tert-butoxyphenyl)propane, 2,2-bis(4'-tert-butoxycarbonyloxyphenyl)propane, 2,2-bis(4'-tert-butoxycarbonylmethyloxyphenyl)propane, 2,2-bis[4'-(1''-ethoxyethoxy)phenyl]propane, 2,2-bis[4'-(1''-ethoxypropyloxy)phenyl]propane, tert-butyl 4,4-bis[4'-(2''-tetrahydropyranyloxy)phenyl]valerate, tert-butyl 4,4-bis[4'-(2''-tetrahydrofuranyloxy)phenyl]valerate, tert-butyl 4,4-bis (4'-tert-butoxyphenyl)valerate, tert-butyl 4,4-bis(4'-tert-butoxycarbonyloxyphenyl)valerate, tert-butyl 4,4-bis(4'-tert-butoxycarbonylmethyloxyphenyl)valerate, tert-butyl 4,4-bis[4'-(1''-ethoxyethoxy)phenyl]valerate, tert-butyl 4,4-bis[4'-(1''-ethoxypropyloxy)phenyl]valerate, tris[4-(2'-tetrahydropyranyloxy)phenyl]methane, tris[4-(2'-tetrahydrofuranyloxy)phenyl]methane, tris(4-tert-butoxyphenyl) methane, tris(4-tert-butoxycarbonyloxyphenyl)methane, tris (4-tert-butoxycarbonyloxymethylphenyl)methane, tris[4-(1'-ethoxyethoxy)phenyl]methane, tris[4-(1'-ethoxypropyloxy)phenyl]methane, 1,1,2-tris[4'-(2''-tetrahydropyranyloxy)phenyl]ethane, 1,1,2-tris[4'-(2''-tetrahydrofuranyloxy)phenyl]ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris[4'-(1''-ethoxyethoxy)phenyl]ethane, and 1,1,2-tris[4'-(1''-ethoxypropyloxy)phenyl]ethane.

The dissolution inhibitor (G) may be added to the resist material of the invention comprising as a photoacid generator the sulfonyldiazomethane represented by formula (1), (1a), (1a') or (1a'') preferably in an amount of 20 parts by weight or less, more preferably 15 parts by weight or less per 100 parts by weight of the solid content in the resist material. Amounts exceeding 20 parts by weight may deteriorate the heat resistance of the resist material because of an increase in the content of the monomer components.

The sulfonyldiazomethane of the invention represented by formula (1), (1a), (1a') or (1a'') can be used as a photoacid generator for chemical amplification negative resist materials. Examples of the alkali soluble resin of component (H) include, but not limited to, intermediates of the component (A). Examples include, but not limited to, poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated poly(p-hydroxystyrene) copolymer, poly(p-hydroxystyrene-α-methyl-p-hydroxystyrene) copolymer, poly(p-hydroxystyrene-α-methylstyrene) copolymer, poly(p-hydroxystyrene-styrene) copolymer, poly(p-hydroxystyrene-m-hydroxystyrene) copolymer, poly(p-hydroxystyrene-styrene) copolymer, poly(p-hydroxystyrene-acrylic acid) copolymer, poly(p-hydroxystyrene-methacrylic acid) copolymer, poly(p-hydroxystyrene-methyl acrylate) copolymer, poly(p-hydroxystyrene-acrylic acid-methyl methacrylate) copolymer, poly(p-hydroxystyrene-methyl methacrylate) copolymer, poly(p-hydroxystyrene-methacrylic acid-methyl methacrylate) copolymer, poly(methacrylic acid), poly (acrylic acid), poly(acrylic acid-methyl acrylate) copolymer, poly(methacrylic acid-methyl methacrylate) copolymer, poly(acrylic acid-maleimide) copolymer, poly(methacrylic acid-maleimide) copolymer, poly(p-hydroxystyrene-acrylic acid-maleimide) copolymer, and poly(p-hydroxystyrene-methacrylic acid-maleimide) copolymer.

Preferred are poly(p-hydroxystyrene), partially hydrogenated poly(p-hydroxystyrene) copolymer, poly(p-hydroxystyrene-styrene) copolymer, poly(p-hydroxystyrene-acrylic acid) copolymer, and p-hydroxystyrene-methacrylic acid) copolymer.

Alkali soluble resins having the following unit (2), (2'), (2'') or (2''') are especially preferred.

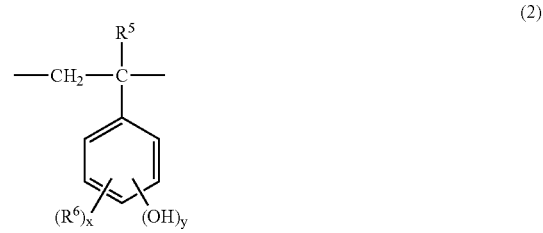

(2)

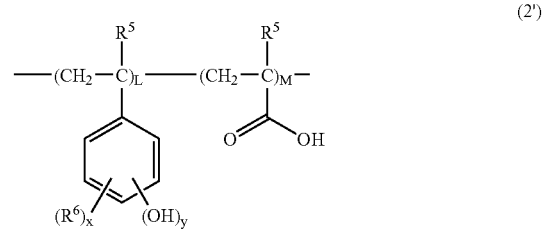

(2')

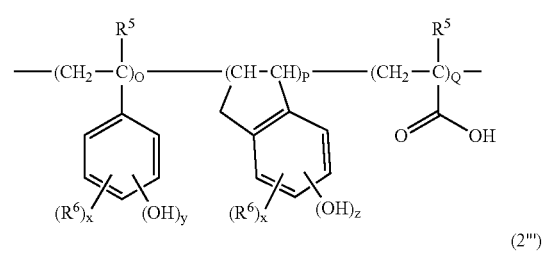

(2'')

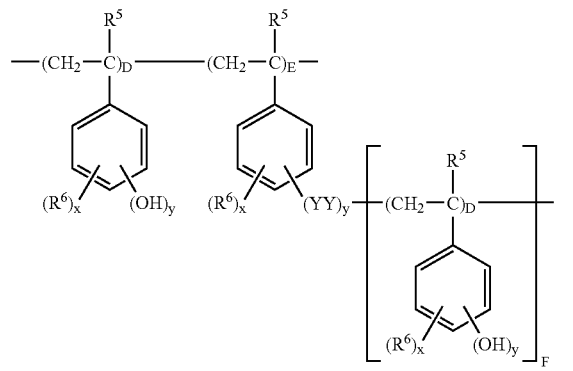

(2''')

Herein, $R^5$ represents a hydrogen atom or a methyl group; $R^6$ represents a linear, branched or cyclic $C_{1-8}$ alkyl group; x stands for 0 or a positive integer and y stands for a positive integer, satisfying x+y≦5 L and M stand for a positive integer, satisfying 0<M/(L+M)≦0.5; O and P stand for a positive integer and Q stands for 0 or a positive integer, satisfying 0<P/(O+P+Q)≦0.5; YY represents a divalent organic group selected from $CH_2$, CH(OH), $CR^6$(OH), C=O and $C(OR^6)$(OH), or a trivalent organic group represented by —C(OH)=; Ds may be same or different and each stands for a positive integer, and E stands for a positive integer, satisfying E/(D+E)= from 0.001 to 0.1; and F stands for 1 or 2.

The polymer preferably has a weight-average molecular weight of from 3,000 to 100,000. The polymers having a molecular weight less than 3000 may be inferior in the capacity as a polymer, and tend to have low heat resistance and insufficient film forming properties. Those having a molecular weight exceeding 10,000, on the other hand, may have problems in solubility in a developer and in a resist solvent owing to an excessively large molecular weight.

The dispersity may be preferably 3.5 or less, more preferably 1.5 or less. The dispersity exceeding 3.5 tends to lead to deterioration in resolution. Although no particular limitation is imposed on the preparation process, a polymer having low dispersity (narrow dispersion) can be synthesized by adopting living anion polymerization for poly-p-hydroxystyrene.

In order to impart various functions, a substituent may be introduced into part of the phenolic hydroxyl group or carboxyl group of the polymer protected with the acid-labile group. For example, it is preferred to introduce a substituent for improving the adhesion with a substrate or improving the etching resistance, particularly, a substituent relatively stable to an acid or alkali for suppressing an excessive rise in the dissolution rate in an alkali developer at unexposed and low exposed areas. Examples of the substituent include, but not limited to, 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isoboronyl, and cyclohexyl. It is also possible to introduce an acid-decomposable substituent such as tert-butoxycarbonyl group or a relatively acid-undecomposable substituent such as tert-butyl and tert-butoxycarbonylmethyl.

In the resist material of the invention, the resin (H) may be added in any desired amount, preferably in an amount of from 65 to 99 parts by weight, more preferably from 70 to 98 parts by weight per 100 parts by weight of the solid content in the resist material.

As the acid crosslinking agent (I) capable of forming a crosslink structure by the action of an acid, compounds having in the molecule thereof at least two groups selected from hydroxymethyl, alkoxymethyl, epoxy and vinyl ether groups can be mentioned. Substituted glycoluril derivatives, urea derivatives, and hexa(methoxymethyl)melamine compounds are preferred as the acid crosslinking agent of the chemical amplification negative resist material comprising the sulfonyldiazomethane of the invention. Examples include N,N',N'-tetramethoxymethylurea, hexamethoxymethylmelamine, tetrahydroxymethyl-substituted glycolurils and tetraalkoxymethyl-substituted glycolurils such as tetramethoxymethylglycoluril, substituted or unsubstituted bis(hydroxymethylphenol)s and condensates between a phenol compound such as bisphenol A with epichlorohydrin. Especially preferred acid crosslinking agents are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl bisphenol A, 1,4-bis[2-(2-hydroxypropyl)]-benzene, N,N,N',N'-tetramethoxymethylurea, and hexamethoxymethylmelamine. These crosslinking agents may be used singly or in combination of two or more.

Although the acid crosslinking agent as component (I) for forming a crosslink structure by the action of an acid may be added in any desired amount, it is added preferably in an amount of from 1 to 20 parts by weight, more preferably from 5 to 15 parts by weight, per 100 parts by weight of the solid content in the resist material.

Although no particular limitation is imposed on the alkali soluble compound as component (J) having a molecular weight not greater than 2500, those having at least two of phenol and/or carboxyl groups are preferred. Specific examples include cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl) valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used singly or in combination of two or more.

Although the alkali-soluble compound as component (J) having a molecular weight not greater than 2500 may be added in any desired amount, it may be added preferably in an amount of from 0 to 20 parts by weight, more preferably from 2 to 10 parts by weight per 100 parts by weight of the solid content in the resist material.

In the chemical amplification resist material of the invention, additives such as surfactant for improving application properties or a light absorbing material for reducing diffuse reflection from the substrate can be incorporated further.

Examples of the surfactant include, but not particularly limited to, nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorine surfactants such as "EFTOP EF301, EF303 and EF352 (each, trade name; product of Tohkem Products Co., Ltd.), "Megaface F171, F172 and F173" (each, trade name; product of Dai-Nippon Ink & Chemicals, Inc.), "Florade FC430 and FC431" (each, trade name; product of Sumitomo 3M Co., Ltd.), and "Aashiguard AG710, Surflon S-381, S-382, SC101, SC102, SC103, SC104, SC105, SC106, Surfynol E1004, KH-10, KH-20, KH-30 and KH-40" (each, trade name; product of Asahi Glass Co., Ltd.); organosiloxane polymers "KP341, X-70-092 and X-70-093" (each, trade name; product of Shin-Etsu Chemical Co., Ltd.), and acrylic acid or-methacrylic acid surfactants such as "Polyflow No. 75 and No. 95" (each, product of Kyoeisha Chemical Co., Ltd.). Of these, FC430, Surflon S-381, Surfynol E1004, KH-20 and KH-30 are preferred. These surfactants may be used singly or in combination of two or more.

The surfactant may be added to the chemical amplification resist material of the invention preferably in an amount of 2 parts by weight or less, more preferably 1 part by weight or less per 100 parts by weight of the solid content of the resist material composition.

In the chemical amplification resist material of the invention, a UV absorber may be incorporated. Although no particular limitation is imposed on it, those as described in Japanese Patent Application Unexamined Publication No. 11-190904/1999 can be used. Preferred examples include diaryl sulfoxide derivatives such as bis(4-hydroxyphenyl) sulfoxide, bis(4-tert-butoxyphenyl)sulfoxide, bis(4-tert-butoxycarbonyloxyphenyl)sulfoxide, and bis[4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazide-containing compounds such as complete or partial ester compounds between naphthoquinone-1,2-diazide-5-sulfonic acid chloride and 2,3,4-trihydroxybenzophenone and complete or partial ester compounds between naphthoquinone-1,2-diazide-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate.

Addition of the UV absorber is not essential and the UV absorber may or may not be added, depending on the kind of the resist material. When it is added, its amount may range from 0 to 10 parts by weight, more preferably from 0.5 to 10 parts by weight, still more preferably from 1 to 5 parts by weight per 100 parts by weight of the base resin.

When the chemical amplification resist material of the invention comprising the sulfonyldiazomethane represented by formula (1), (1a), (1a') or (1a") and the resin which changes its solubility in an alkali developer by the action of an acid is used for the fabrication of a variety of integrated circuits, known lithography technique can be employed without particular limitation to it.

A description will next be made of the patterning process of the invention based on a preferred condition. It should, however, be borne in mind that the invention is not limited to it.

The resist material may be applied onto a substrate (such as Si, $SiO_2$, SiN, SiON, TiN, WSi, BPSG, SOG, organic anti-reflecting film) for the fabrication of integrated circuits by a suitable application method such as spin coating, roll coating, flow coating, dip coating, spray coating or doctor coating to give a film thickness of from 0.1 to 2.0 μm. The coating may be prebaked on a hot plate at 60 to 150° C. for about 1 to 10 minutes, preferably 80 to 120° C. for 1 to 5 minutes.

Through a predetermined mask, the prebaked coating may be then exposed to a light source selected from UV, deep-UV, electron beam, X-ray, excimer laser light, γ-ray and synchrotron radiation, preferably to an exposure wavelength not greater than 300 nm. Exposure may be performed so as to give an exposure dose of about 1 to 200 $mJ/cm^2$, preferably about 10 to 100 $mJ/cm^2$.

If necessary, the coating may be subjected to post exposure bake (PEB) on a hot plate at 60 to 150° C. for 1 to 5 minutes, preferably 80 to 120° C. for 1 to 3 minutes. This heating is required when, for example, dissociation reaction of the acid-labile group hardly occurs without heating and therefore sufficient resolution cannot be attained.

The coating may be then developed while using as a developer an aqueous alkali solution, for example, a 0.1 to 5 wt %, preferably 2 to 3 wt % aqueous solution of tetramethylammonium hydroxide (TMAH) for 0.1 to 3 minutes, preferably for 0.5 to 2 minutes in a conventional manner such as dipping, puddling or spraying, whereby an intended pattern is formed on the substrate. The material of the invention may be best suited for micro-patterning using high energy radiation such as deep UV with a wavelength of 254 to 193 nm, vacuum UV with a wavelength of 157 nm, electron beam, x-ray, excimer laser light, y-ray and synchrotron radiation. Outside the above-described range, the intended pattern may not be formed.

EXAMPLES

The invention will hereinafter be described in detail by Synthesis Examples and Examples. It should, however, be borne in mind that the invention is not limited to or by them.

Synthesis Example 1

Synthesis of ((4-(1,3-dioxolan-2-yl)-1-hydroxycyclohexyl)methyl)trimethylsilane

A Grignard reagent was prepared in a conventional manner by using 44.6 g (0.36 mole) of (chloromethyl)trimethylsilane, 8.8 g (0.36 mole) of metal magnesium and 194 g of diethyl ether. To the resulting Gignard reagent was added 50.9 g (0.33 mole) of 1,4-cyclohexanedione monoketal over an ice bath at a temperature below 20° C. After stirring for 2 hours at 40° C., 125 g of water was added to the resulting mixture over an ice bath. The supernatant thus separated was collected, and washed with 200 g of saturated sodium chloride water. The solvent was removed under reduced pressure, whereby 77.6 g of ((4-(1,3-dioxolan-2-yl)-1-hydroxycyclohexyl)methyl)trimethylsilane was obtained.

Synthesis Example 2

Synthesis of 1-(1,3-dioxolan-2-yl)-4-methylenecyclohexane

After 15.7 g (0.39 mole) of sodium hydride was washed with n-hexane, it was suspended in 199 g of tetrahydrofuran. A solution obtained by dissolving the above hydroxysilane in 112 g of tetrahydrofuran was added dropwise, followed by aging for 41 hours under heating and reflux. After 140 g of water was added to terminate the reaction, the organic phase was obtained by separation. The resulting organic phase was washed with 60 g of saturated sodium chloride water. The solvent was then removed under reduced pressure, whereby the target 1-(1,3-dioxolan-2-yl)-4-methylenecyclohexane was obtained (two step yield: 77%). Gas chromatography revealed that its purity was 83%.

Synthesis Example 3

Synthesis of S-((4-(1,3-dioxolan-2-ylcyclohexyl)methyl)thioacetate

In 188 g of tetrahydrofuran was dissolved 46.8 g (0.25 mole) of the above methylenecyclohexane. Thioacetic acid (22.0 ml, 0.31 mole) was added dropwise to the resulting solution at a speed slow enough not to increase the internal temperature, followed by aging for 1 hour. After further addition of 3.5 ml (0.05 mole) of thioacetic acid and aging for 30 minutes, 200 g of a saturated aqueous solution of sodium bicarbonate was added to terminate the reaction. The organic phase obtained by separation of the reaction mixture was washed with 50 g of saturated sodium chloride water. The solvent was then removed under reduced pressure, whereby 76.7 g of the target S-((4-(1,3-dioxolan-2-ylcyclohexyl)methyl)thioacetate was obtained.

Synthesis Example 4

Synthesis of (4-(1,3-dioxolan-2-yl)cyclohexyl)methanethiol

In 239 g of methanol was dissolved 76.7 g of the above S-(cyclohexyl)methyl thioacetate. A solution obtained by dissolving 11.3 g (0.28 mole) of sodium hydroxide in 77 g of water was added to the resulting solution, followed by aging for 30 minutes. To the reaction mixture was added 230 g of water and methanol was removed under reduced pressure. A solution obtained by diluting 27.8 g of concentrated hydrochloric acid (12N) with 60 g of water was added to the residue and the resulting acidic solution was extracted with 150 g of diethyl ether. After the organic phase thus obtained was washed with 40 g of saturated sodium chloride water, the solvent was removed under reduced pressure, whereby 46.7 g of the target (4-(1,3-dioxolan-2-yl)cyclohexyl)methanethiol was obtained (two step yield: 78%). Gas chromatography revealed that its purity was 78%.

Synthesis Example 5

Synthesis of bis((4-(1,3-dioxolan-2-yl)cyclohexyl)methylsulfenyl)methane

In 97 g of ethanol were dissolved 48.7 g (0.23 mole) of the above cyclohexylmethanethiol, 9.7 g (0.24 mole) of sodium hydroxide, and 12.4 g (0.15 mole) of dichloromethane. The resulting solution was heated to 60° C. over a water bath, followed by aging for 2 hours. After the reaction mixture was allowed to cool down to room temperature, 216 g of water was added. The organic phase was collected, whereby 51.0 g of the target bis((4-(1,3-dioxolan-2-yl)cyclohexyl)methylsulfenyl)methane was obtained.

Synthesis Example 6

Synthesis of bis((4-1,3-dioxolan-2-yl)cyclohexyl)methylsulfonyl)methane

To 17.7 g (0.23 mole) of ammonium acetate and 153 g of ethanol were added 51.0 g (0.11 mole) of the above bissulfenylmethane and 1.1 g (0.0034 mole) of sodium tungstate dihydrate. The resulting mixture was heated over an oil bath to 75° C. and 54.7 g (0.56 mole) of aqueous hydrogen peroxide was added dropwise at a temperature below 80° C. After aging for 2.5 hours at this temperature, 14.0 g (0.14 mole) of aqueous hydrogen peroxide was added further and aging was performed for 1 hour. Water (174 g) was then added and the mixture was cooled over an ice bath. White crystals then precipitated. The resulting crystals were collected by filtration, whereby 28.1 g of the target bis((4-(1,3-dioxolan-2-yl)cyclohexyl)methylsulfonyl)methane was obtained (two step yield: 55%).

Synthesis Example 7

Synthesis of bis((4-(1,3-dioxolan-2-yl)cyclohexyl)methylsulfonyl)diazomethane In 45 g of dichloromethane were dissolved 5.0 g (0.011 mole) of the above bissulfonylmethane and 3.7 g (0.019 mole) of p-toluenesulfonyl azide. After cooling over an ice bath, 1.7 ml (0.011 mole) of diazabicyclo[5,4,0]-7-undecene (DBU) was added dropwise at a temperature below 5° C., followed by aging for 15 minutes. The reaction was terminated by the addition of 28 g of water and 7 g of concentrated hydrochloric acid (12N). The organic phase was collected. The organic phase was washed with 30 g of water and then the solvent was removed under reduced pressure, whereby a crude product was obtained as an oil. The oil was purified by recrystallization, whereby 2.2 g of the target bis((4-(1,3-dioxolan-2-yl)cyclohexyl)methylsulfonyl)diazomethane was obtained (yield: 42%).

The following are the results of NMR and IR of the resulting bis((4-(1,3-dioxolan-2-yl)cyclohexyl)methylsulfonyl)diazomethane.

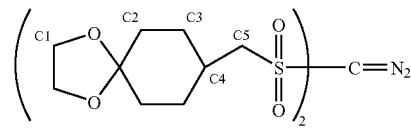

$^1$HNMR (CDCl$_3$): δ (ppm) 1.55 (m, 8H, C2, C3-H), 1.75 (m, 4H, C3-H), 1.94 (m, 4H, C2-H), 2.08 (m, 2H, C4-H), 3.40 (d, 4H, J=6.3 Hz, C5-H), 3.92 (t, 8H, J=2.7 Hz, C1-H). IR (KBr): ν (cm$^{-1}$) 2981, 2942, 2869, 2125, 1349, 1340, 1330, 1319, 1205, 1133, 1103, 1012, 925, 657, 611, 576.

Synthesis Example 8

Synthesis of ((4-(1,3-dioxolan-2-yl)-1-hydroxycyclohexyl)methyl)trimethylsilane A Wittig reagent was prepared in a conventional manner by using 272.4 g (0.66 mole) of n-pentyltriphenylphosphonium bromide, 74.1 g (0.66 mole) of potassium t-butoxide and 408.5 g of tetrahydrofuran. To the resulting Wittig reagent was added 70.6 g (0.45 mole) of 1,4-cyclohexanedione monoketal over an ice bath at a temperature below 20° C. After stirring for 2 hours at room temperature, the reaction mixture was poured into 200 g of ethyl acetate and 200 g of water to collect the organic phase. The resulting organic phase was washed with 100 g of saturated sodium chloride water and the solvent was removed under reduced pressure. By distillation under reduced pressure, 46.8 g of the target 1-(1,3-dioxolan-2-yl)-4-pentenylidenecyclohexane was obtained (yield: 90%). Gas chromatography revealed that its purity was 99%.

Synthesis Example 9

Synthesis of bis(n-butyl(4-(1,3-dioxolan-2-yl)cyclohexyl)methylsulfonyl)diazomethane In a similar manner to Synthesis Examples 3 to 7 except for the use of 1-(1,3-dioxolan-2-yl)-4-pentenylidenecylohexane instead of the 1-(1,3-dioxolan-2-yl)-4-methylenecylohexane of Synthesis Example 3, the target bis(n-butyl(4-(1,3-dioxolan-2-yl)cyclohexyl)methylsulfonyl) diazomethane was obtained. The followings are the results of NMR and IR of the resulting bis(n-butyl(4-(1,3-dioxolan-2-yl)cyclohexyl)methylsulfonyl)diazomethane.

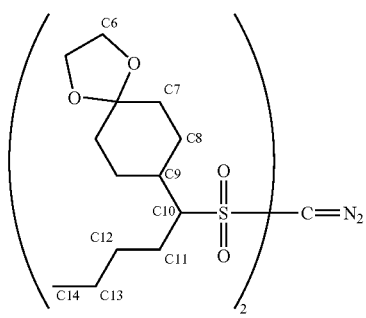

$^1$HNMR (CDCl$_3$): δ (ppm) 0.92 (t, 6H, J=7.2 Hz, C14-H), 1.66 (m, 28H, C7, C8, C11, C12, C13-H), 1.94 (m, 4H, C2-H), 2.12 (m, 2H, C9-H), 3.47 (dt, 4H, J=2.5, 6.0 Hz, C10-H), 3.92 (brs, 8H, C6-H). IR (KBr): ν (cm$^{-1}$) 2954, 2873, 2117, 1448, 1338, 1230, 1133, 1103, 1035, 970, 611, 588, 543.

Synthesis Example 10

Synthesis of bis(n-butyl(cyclohexyl)methylsulfonyl)diazomethane

In a similar manner to Synthesis Examples 3 to 8 except for the use of cyclohexanone instead of the 1,4-cyclohexanedione monoethylene ketal of Synthesis Example 8, the target bis(n-butyl(cyclohexyl)methylsulfonyl)diazomethane was obtained. The followings are the results of NMR and IR of the resulting bis(n-butyl(cyclohexyl)methylsulfonyl)diazomethane.

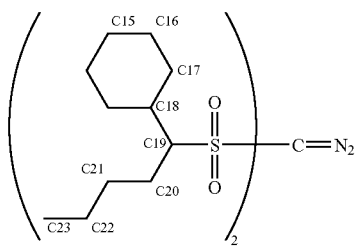

$^1$HNMR (CDCl$_3$): δ (ppm) 0.93 (t, 6H, J=7.3 Hz, C23-H), 1.33 (m, 18H, C15, C16, C20, C21, C22-H), 1.70 (m, 14H, C15, C16, C17-H), 2.14 (m, 2H, C18-H), 3.42 (dt, 4H, J=2.6, 6.0Hz, C19-H). IR (KBr): ν (cm$^{-1}$) 2931, 2856, 2107, 1467, 1452, 1338, 1322, 1238, 1135, 968, 582.

Synthesis Example 11

Synthesis of bis((tert-butylcyclohexyl)methylfulonyl)diazomethane

In a similar manner to Synthesis Examples 3 to 8 except for the use of 4-tert-butylcyclohexanone instead of the 1,4-cyclohexanedione monoethylene ketal of Synthesis Example 8, the target bis((tert-butylcyclohexyl)methylfulonyl)diazomethane was obtained. The followings are the results of NMR and IR of the resulting bis((tert-butylcyclohexyl)methylfulonyl)diazomethane.

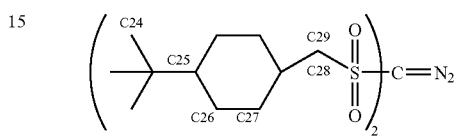

$^1$HNMR (CDCl$_3$): δ (ppm) 0.83 (s, 18H, C24-H), 1.05 (m, 10H, C25, 26, 27-H), 1.80 (m, 4H, C26-H), 1.99 (m, 6H, C27, 28-H), 3.36 (d, 4H, J=6.0 Hz, C29-H). IR (KBr): ν (cm$^{-1}$) 2942, 2861, 2130, 2113, 1363, 1346, 1322, 1236, 1139, 998, 987, 765, 659, 605, 578, 528.

Examples 1 to 24 and Comparative Examples 1 to 3

Resist materials shown in Tables 1 to 3 were prepared. Components of the resist materials shown in Tables 1 to 3 are as follows:

Polymer A: poly(p-hydroxystyrene) having hydroxyl groups protected with 15 mole % of 1-ethoxyethyl groups and 15 mole % of tert-butoxycarbonyl groups and having a weight-average molecular weight of 12,000.

Polymer B: poly(p-hydroxystyrene) having hydroxyl groups protected with 30 mole % of 1-ethoxyethyl groups and having a weight-average molecular weight of 12,000.

Polymer C: poly(p-hydroxystyrene) having hydroxyl groups protected with 25 mole % of 1-ethoxyethyl groups and crosslinked with 3 mole % of 1,2-propanediol divinyl ether and having a weight-average molecular weight of 13,000.

Polymer D: poly(p-hydroxystyrene) having hydroxyl groups protected with 28 mole % of tert-pentyl groups and having a weight-average molecular weight of 8,000.

Polymer E: p-hydroxystyrene/2-ethyl-2-adamantyl acrylate copolymer having a compositional ratio (molar ratio) of 70:30 and a weight-average molecular weight of 15,000.

Polymer F: p-hydroxystyrene/1-ethyl-1-norbornene methacrylate copolymer having a compositional ratio (molar ratio) of 70:30 and a weight-average molecular weight of 15,000.

Polymer G: p-hydroxystyrene/tert-butyl acrylate copolymer having a compositional ratio (molar ratio) of 65:35 and a weight-average molecular weight of 15,000.

Polymer H: p-hydroxystyrene/1-ethylcyclopentyl methacrylate copolymer having a compositional ratio (molar ratio) of 65:35 and a weight-average molecular weight of 15,000.

Polymer I: p-hydroxystyrene/1-ethylcyclopentyl methacrylate/p-tert-pentyloxystyrene copolymer having a compositional ratio (molar ratio) of 70:8:22 and a weight-average molecular weight of 16,000.

Polymer J: p-hydroxystyrene/1-ethylcyclopentyl methacrylate/styrene copolymer having a compositional ratio (molar ratio) of 65:10:25 and a weight-average molecular weight of 12,000.

Polymer K: p-hydroxystyrene/indene copolymer having a compositional ratio (molar ratio) of 80:20, in which the hydroxyl groups of hydroxystyrene have been protected with 20 mol % of tert-butoxycarbonyl groups, and having a weight-average molecular weight of 10,000.

Polymer L: p-hydroxystyrene/indene/2-ethyl-2-adamantyl methacrylate copolymer having a compositional ratio (molar ratio) of 82:4:14 and a weight-average molecular weight of 8,000.

Polymer M: p-hydroxystyrene/indene/1-ethyl-1-norbornene methacrylate copolymer having a compositional ratio (molar ratio) of 84:4:12 and a weight-average molecular weight of 8,000.

Polymer N: poly(p-hydroxystyrene) having hydroxyl groups protected with 8 mole % of acetyl groups and having a weight-average molecular weight of 8,000.

PAG1: bis(4-methoxyphenylsulfonyl)diazomethane
PAG2: bis(4-methylphenylsulfonyl)diazomethane
PAG3: bis(2,4-dimethylphenylsulfonyl)diazomethane
PAG4: (4-tert-butoxyphenyl)diphenylsulfonium 10-camphorsulfonate
PAG5: Compound of Synthesis Example 7
PAG6: Compound of Synthesis. Example 9
PAG7: Compound of Synthesis Example 10
PAG8: Compound of Synthesis Example 11
PAG9: bis(cyclohexylsulfonyl)diazomethane
PAG10: N-10-camphorsulfonyloxysuccinimide
Crosslinker A: 1,3,5,7-tetramethoxymethylglycoluril
Dissolution inhibitor: bis(4-(2'-tetrahydropyranyloxy)phenyl)methane
Basic compound A: tri-n-butylamine
Basic compound B: tris(2-methoxyethyl)amine
Organic acid derivative A: 4,4-bis(4'-hydroxyphenyl)valeric acid
Organic acid derivative B: salicylic acid
Surfactant A: FC-430 (Sumitomo 3M Co., Ltd.)
Surfactant B: Surflon S-381 (Asahi Glass Co., Ltd.)
UV absorber: 9,10-dimethylanthracene
Solvent A: propylene glycol methyl ether acetate
Solvent B: ethyl lactate After the resist materials thus obtained were each filtered through a 0.2-μm Teflon™ filter, the resist solution was spin-coated to give a thickness of 0.6 μm onto a silicon wafer to which an organic antireflection film ("DUV-44", trade name; product of Brewer Science) had been applied with a thickness of 800 Å. The silicon wafer was then baked for 90 seconds on a hot plate of 100° C. The resist film was exposed to ⅔ annular illumination using an excimer laser stepper ("NSR-S202A", trade name; product of Nikon Corp., NA=0.6), baked (PEB: post exposure bake) at 110° C. for 90 seconds, and developed with a 2.38% aqueous solution of tetramethylammonium hydroxide, whereby positive patterns (Examples 1-23, Comparative Examples 1-3) or negative pattern (Example 24) was obtained. In this application step and the subsequent baking and developing steps, a coater/developer ("Clean Track Act 8", trade name; product of Tokyo Electron Co., Ltd.) was used.

The resulting resist patterns were evaluated as described below.

Resist Pattern Evaluation Method

Supposing that the exposure dose permitting a 1:1 resolution at the top and bottom of a 0.18-μm line-and-space pattern was the optimum exposure dose (sensitivity: Eop), the minimum line width of a line-and-space pattern which was separated at this dose was considered as the resolution of a resist to be evaluated. In addition, the cross-sectional view of the resist pattern after resolution was observed under a scanning electron microscope. A resist capable of keeping, in spite of the offsetting of a focal point, the film thickness of the resist pattern at 80% of that when the focal point is not offset while keeping the rectangular form of the pattern shape was judged effective. Then, the depth of focus (DOF) was determined.

The PED stability of a resist was evaluated by a variation in line width after exposing the resist at the optimum exposure dose, allowing it to stand for 24 hours and then carrying out PEB (post exposure bake). The less the variation, the greater is the PED stability.

The evaluation results of the resist pattern are shown in Table 4.

Evaluation Method Other than Pattern Evaluation

The solubility of a resist material in a mixed solvent was judged by visual observation and clogging upon filtration.

The application properties were rated by the presence or absence of uneven coating and variations in the coating thickness. The former one was visually judged. With respect to the latter one, a film gage ("Lambda-Ace VM-3010", trade name of an optical interference film gage, product of Dainippon Screen Mfg. Co., Ltd.) was used to measure the thickness of a resist film on the same wafer at different positions. Based on the measurement results, a variation from the desired coating thickness (0.6 μm) was calculated. The application properties were rated "good" when the variation was within 0.5% (that is, within 0.003 μm), "a little poor" when the variation was greater than 0.5% but within 1%, and "poor" when the variation exceeded 1%.

Storage stability was judged based on the precipitation of foreign matters or sensitivity change with the passage of time. The resist material was rated good when the number of particles having a particle size of 0.3 μm or greater contained in 1 ml of a resist solution was 5 or less after 100 days storage at the maximum as measured by a particle counter ("KL-20A", trade name; product of Rion Co., Ltd.); or when variations in sensitivity (the above-described Eop) compared with that just after preparation was within 5%. The resist material outside the above-described ranges was rated poor.

Foreign matters appearing on the developed pattern were observed under a scanning electron microscope (TDSME: "S-7280H", trade name, product of Hitachi Ltd.). When the number of the foreign matters visually observed within an area of 100 μm² was 10 or less, the material was rated good, when the number was 11 or greater but not greater than 15, the material was rated a little poor and when the number was 16 or greater, the material was rated poor.

Foreign matters after resist peeling were observed using a surface scanner ("Surf-Scan 6220", product of Tencor Instruments). A resist wafer not subjected to pattern exposure but subjected to entire exposure was treated in an ordinary manner, and developed with a 2.38 wt % aqueous solution of tetramethylammonium hydroxide, followed by peeling of the resist film (only the resist film in the exposed area was peeled). When the number of foreign matters having a size of 0.20 μm or greater left on an 8-inch-wafer after resist peeling was 100 or less, the material was rated good; when the number was 101 or greater but not greater than 150, it was rated a little poor and when the number was 151 or greater, the material was rated poor.

The above-described results are shown in Table 5.

TABLE 1

| Example | polymer (wt part) | acid generator (wt part) | cross-linking agent (wt part) | dissolution inhibitor (wt part) | basic compound (wt part) | organic acid derivative (wt part) | surfactant (wt part) | UV absorbent (wt part) | solvent (wt part) |
|---|---|---|---|---|---|---|---|---|---|
| 1 | PolymerA (80) | PAG3 (2) PAG5 (2) | | | comp. A (0.3) | | surfac. A (0.25) | | solv. A (385) |
| 2 | PolymerB (80) | PAG1 (2) PAG6 (1) PAG7 (2) | | | comp. A (0.3) | | surfac. A (0.25) | | solv. A (385) |
| 3 | PolymerC (80) | PAG4 (2) PAG5 (1) PAG8 (2) PAG9 (1) | | | comp. A (0.3) | | surfac. A (0.25) | | solv. A (385) |
| 4 | PolymerD (80) | PAG1 (2) PAG4 (2) PAG5 (1) PAG7 (2) PAG8 (1) PAG10 (1) | | | comp. A (0.3) | | surfac. B (0.25) | | solv. A (385) |
| 5 | PolymerE (80) | PAG2 (2) PAG7 (1) | | | comp. A (0.3) | deriv. A (0.5) | surfac. B (0.25) | | solv. A (385) |
| 6 | PolymerF (80) | PAG1 (2) PAG5 (1) | | | comp. A (0.15) comp. B (0.15) | | surfac. B (0.25) | | solv. A (385) |

TABLE 2

| Example | polymer (wt part) | acid generator (wt part) | cross-linking agent (wt part) | dissolution inhibitor (wt part) | basic compound (wt part) | organic acid derivative (wt part) | surfactant (wt part) | UV absorbent (wt part) | solvent (wt part) |
|---|---|---|---|---|---|---|---|---|---|
| 7 | PolmerG (80) | PAG3 (2) PAG5 (1) PAG9 (1) | | | comp. B (0.3) | deriv. B (0.5) | surfac. B (0.25) | | solv. A (385) |
| 8 | PolymerH (80) | PAG1 (1) PAG3 (1) PAG8 (2) | | | comp. B (0.3) | | surfac. B (0.25) | | solv. A (280) solv. B (105) |
| 9 | PolymerI (80) | PAG1 (2) PAG7 (2) | | | comp. B (0.3) | deriv. A (0.5) | surfac. A (0.25) | | solv. A (385) |
| 10 | PolymerJ (80) | PAG3 (1) PAG6 (2) PAG10 (1) | | | comp. B (0.3) | deriv. A (0.5) | surfac. A (0.25) | | solv. A (385) |
| 11 | PolymerK (80) | PAG4 (2) PAG5 (4) | | | comp. A (0.3) | | surfac. A (0.25) | | solv. A (280) solv. B (105) |

TABLE 2-continued

| Example | polymer (wt part) | acid generator (wt part) | cross-linking agent (wt part) | dissolution inhibitor (wt part) | basic compound (wt part) | organic acid derivative (wt part) | surfactant (wt part) | UV absorbent (wt part) | solvent (wt part) |
|---|---|---|---|---|---|---|---|---|---|
| 12 | PolymerL (80) | PAG2 (2) PAG6 (2) | | | comp. A (0.3) | | surfac. B (0.25) | | solv. A (385) |
| 13 | PolymerC (40) PolymerK (40) | PAG3 (2) PAG5 (2) PAG8 (1) | | | comp. B (0.3) | | surfac. A (0.25) | | solv. A (280) solv. B (105) |
| 14 | PolymerE (40) PolymerG (40) | PAG3 (2) PAG6 (3) PAG10 (1) | | | comp. B (0.3) | deriv. A (0.5) | surfac. B (0.25) | | solv. A (385) |

TABLE 3

| Example | polymer (wt part) | acid generator (wt part) | cross-linking agent (wt part) | dissolution inhibitor (wt part) | basic compound (wt part) | organic acid derivative (wt part) | surfactant (wt part) | UV absorbent (wt part) | solvent (wt part) |
|---|---|---|---|---|---|---|---|---|---|
| 15 | PolymerA (40) PolymerD (40) | PAG3 (1) PAG4 (2) PAG7 (2) | | | comp. B (0.3) | | surfac. B (0.25) | | solv. A (385) |
| 16 | PolymerD (60) PolymerM (20) | PAG2 (2) PAG6 (1) | | | comp. B (0.3) | deriv. B (0.25) | surfac. B (0.25) | | solv. A (385) |
| 17 | PolymerL (40) PolymerM (40) | PAG3 (2) PAG5 (1) PAG10 (1) | | | comp. B (0.3) | deriv. A (0.5) | surfac. A (0.25) | absorb. (0.5) | solv. A (280) solv. B (105) |
| 18 | PolymerC (40) PolymerD (40) | PAG2 (2) PAG5 (5) | | | comp. A (0.3) | | surfac. B (0.25) | | solv. A (385) |
| 19 | PolymerE (10) PolymerL (70) | PAG2 (2) PAG4 (2) PAG8 (1) | | | comp. A (0.3) | | surfac. A (0.25) | | solv. A (385) |
| 20 | PolymerB (60) PolymerI (20) | PAG1 (2) PAG7 (2) | | | comp. B (0.3) | | surfac. A (0.25) | | solv. A (385) |
| 21 | PolymerD (70) PolymerI (10) | PAG4 (2) PAG6 (3) | | | comp. A (0.15) comp. B (0.15) | | surfac. A (0.25) | | solv. A (385) |
| 22 | PolymerA (60) PolymerL (20) | PAG1 (2) PAG8 (2) PAG10 (1) | | | comp. A (0.3) | | | | solv. A (280) solv. B (105) |

TABLE 4

| Example | polymer (wt part) | acid generator (wt part) | cross-linking agent (wt part) | dissolution inhibitor (wt part) | basic compound (wt part) | organic acid derivative (wt part) | surfactant (wt part) | UV absorbent (wt part) | solvent (wt part) |
|---|---|---|---|---|---|---|---|---|---|
| 23 | PolymerB (75) | PAG1 (1) PAG3 (2) PAG5 (2) | | dissol. (5) | comp. B (0.3) | | | absorb. A (0.25) | solv. A (280) solv. B (105) |
| 24 | PolymerN (80) | PAG2 (1) PAG3 (1) PAG5 (2) | cross-link. A (20) | | comp. B (0.3) | | | absorb. B (0.25) | solv. A (385) |

TABLE 5

| Comp. Example | polymer (wt part) | acid generator (wt part) | cross-linking agent (wt part) | dissolution inhibitor (wt part) | basic compound (wt part) | organic acid derivative (wt part) | surfactant (wt part) | UV absorbent (wt part) | solvent (wt part) |
|---|---|---|---|---|---|---|---|---|---|
| 1 | polymerA (80) | PAG1 (2) PAG10 (1) | | | comp. A (0.125) | | surfac. A (0.25) | | solv. A (385) |
| 2 | polymerE (80) | PAG2 (2) PAG9 (4) | | | comp. B (0.125) | deriv. A (0.5) | surfac. A (0.25) | | solv. A (385) |
| 3 | polymerA (40) polymerK (40) | PAG3 (2) PAG9 (2) | | | comp. B (0.125) | | surfac. B (0.25) | | solv. A (385) |

TABLE 6 evaluation result of resist pattern

| | sensitivity (mj/cm$^2$) | resolution (μm) | profile shape | DOF of 0.18 μm (μm) | 0.18 μm profile shape* | dimensional stability of PED after 24 hours (nm) |
|---|---|---|---|---|---|---|
| Example 1 | 33 | 0.15 | rectangular | 1.1 | rectangular | −8 |
| Example 2 | 35 | 0.16 | rectangular | 1.1 | rectangular | −8 |
| Example 3 | 32 | 0.15 | rectangular | 1.2 | rectangular | −8 |
| Example 4 | 25 | 0.15 | rectangular | 1.2 | rectangular | −9 |
| Example 5 | 20 | 0.14 | rectangular | 1.2 | rectangular | −8 |
| Example 6 | 38 | 0.16 | rectangular | 1.2 | rectangular | −8 |
| Example 7 | 25 | 0.15 | rectangular | 1.1 | rectangular | −8 |
| Example 8 | 39 | 0.15 | rectangular | 1.0 | rectangular | −8 |
| Example 9 | 29 | 0.16 | rectangular | 1.1 | rectangular | −9 |
| Example 10 | 28 | 0.14 | rectangular | 1.2 | rectangular | −8 |
| Example 11 | 32 | 0.15 | rectangular | 1.1 | rectangular | −8 |
| Example 12 | 31 | 0.15 | rectangular | 1.2 | rectangular | −8 |
| Example 13 | 30 | 0.16 | rectangular | 1.2 | rectangular | −8 |
| Example 14 | 28 | 0.15 | rectangular | 1.1 | rectangular | −8 |
| Example 15 | 35 | 0.16 | rectangular | 1.0 | rectangular | −9 |
| Example 16 | 37 | 0.15 | rectangular | 1.1 | rectangular | −8 |
| Example 17 | 28 | 0.15 | rectangular | 1.1 | rectangular | −8 |
| Example 18 | 35 | 0.14 | rectangular | 1.1 | rectangular | −8 |
| Example 19 | 34 | 0.15 | rectangular | 1.2 | rectangular | −8 |
| Example 20 | 37 | 0.15 | rectangular | 1.1 | rectangular | −8 |
| Example 21 | 32 | 0.14 | rectangular | 1.2 | rectangular | −8 |
| Example 22 | 31 | 0.16 | rectangular | 1.1 | rectangular | −8 |
| Example 23 | 30 | 0.15 | rectangular | 1.1 | rectangular | −8 |
| Example 24 | 29 | 0.18 | rectangular | 1.0 | rectangular | −8 |
| Comp. Ex. 1 | 35 | 0.15 | taper | 0.8 | taper | −9 |
| Comp. Ex. 2 | 38 | 0.15 | round head | 0.8 | round head | −8 |
| Comp. Ex. 3 | 39 | 0.15 | taper | 0.9 | taper | −9 |

*pattern shape when a focal point is shifted to a negative side by 0.4 μm at the measurement of DOF of 0.18 μm.

TABLE 7

| | Evaluation result other than pattern evaluation result | | | | |
|---|---|---|---|---|---|
| | solubility | applicability | storage stability (100 days) | contamination during development | contamination after peeling |
| Example 1 | good | good | good | good | good |
| Example 2 | good | good | good | good | good |
| Example 3 | good | good | good | good | good |
| Example 4 | good | good | good | good | good |
| Example 5 | good | good | good | good | good |
| Example 6 | good | good | good | good | good |
| Example 7 | good | good | good | good | good |
| Example 8 | good | good | good | good | good |
| Example 9 | good | good | good | good | good |
| Example 10 | good | good | good | good | good |
| Example 11 | good | good | good | good | good |
| Example 12 | good | good | good | good | good |
| Example 13 | good | good | good | good | good |
| Example 14 | good | good | good | good | good |
| Example 15 | good | good | good | good | good |
| Example 16 | good | good | good | good | good |
| Example 17 | good | good | good | good | good |
| Example 18 | good | good | good | good | good |
| Example 19 | good | good | good | good | good |
| Example 20 | good | good | good | good | good |
| Example 21 | good | good | good | good | good |
| Example 22 | good | good | good | good | good |
| Example 23 | good | good | good | good | good |
| Example 24 | good | good | good | good | good |
| Comp. Ex. 1 | good | good | 30 days < (change of sensitivity) | poor | a little poor |
| Comp. Ex. 2 | good | good | good | a little poor | poor |
| Comp. Ex. 3 | good | good | good | poor | poor |

The invention claimed is:

1. A sulfonyldiazomethane compound represented by formula (1):

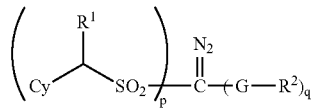

(1)

wherein $R^1$ represents a hydrogen atom or a linear, branched or cyclic, substituted or unsubstituted $C_{1-6}$ alkyl group; Cy represents a cyclohexyl group, a cyclohexyl group having part or all of hydrogen atoms in a ring thereof substituted by a linear, branched or cyclic, unsubstituted $C_{1-6}$ alkyl group only, a cyclohexyl group having part or all of hydrogen atoms in a ring thereof substituted by a linear, branched or cyclic, unsubstituted $C_{1-6}$ alkoxy group, a cyclohexyl group having a carbonyl group in a ring thereof, a cyclohexyl group having a carbonyl group in a ring thereof and having part or all of hydrogen atoms in the ring substituted by a linear, branched or cyclic, substituted or unsubstituted $C_{1-6}$ alkyl or alkoxy group, or a cyclohexyl group with a $C_{0-6}$ alicyclic structure only or with a $C_{0-6}$ heterocyclic structure; G represents $SO_2$ or CO; $R^2$ represents a linear, branched or cyclic, substituted or unsubstituted $C_{1-10}$ alkyl group or a substituted or unsubstituted $C_{6-14}$ aryl group; and p stands for 1 or 2 and q stands for 0 or 1, satisfying p+q=2.

2. The sulfonyldiazomethane compound according to claim 1 which is represented by formula (1a):

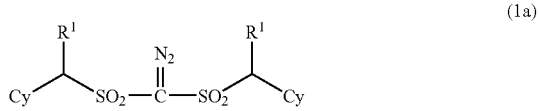

(1a)

wherein the $R^1$s may be the same or different, and the Cy's may be the same or different and represent:
a cyclohexyl group;
a cyclohexyl group having part or all of hydrogen atoms in a ring thereof substituted by a linear, branched or cyclic $C_{1-6}$ alkyl group only;
a cyclohexyl group having part or all of hydrogen atoms in a ring thereof substituted by a linear, branched or cyclic unsubstituted $C_{1-6}$ alkoxy group
a cyclohexyl group having in the ring thereof a carbonyl group; or
a cyclohexyl group with an $C_{0-6}$ alicyclic hydrocarbon structure only;
wherein part or all of the hydrogen atoms in the alkyl group of the above-described cyclohexyl groups may be substituted with a halogen atom.

3. The sulfonyldiazomethane compound according to claim 1 which is represented by formula (1a'):

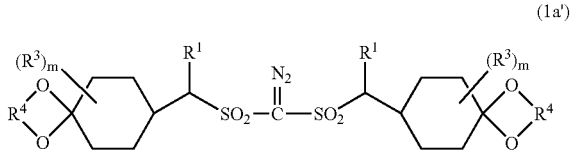

(1a')

wherein the $R^1$s may be same or different; the $R^3$s may be the same or different and each represents a hydrogen atom or a linear, branched or cyclic, substituted or unsubstituted $C_{1-6}$ alkyl group, or a plurality of the $R^3$s may be coupled to form an alicyclic hydrocarbon structure or heterocyclic structure having from 6 to 12 carbon atoms including carbon atoms to which the $R^3$s are bonded; m stands for an integer of 0 to 9; and the $R^4$ may be the same or different and each represents a linear or branched $C_{2-6}$ alkylene group.

4. The sulfonyldiazomethane compound according to claim 1, which is represented by formula (1a''):

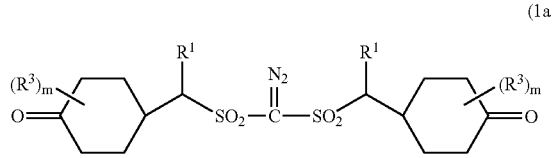

wherein the $R^1$s may be same or different; the $R^3$s may be the same or different and each represents a hydrogen atom or a linear, branched or cyclic, substituted or unsubstituted $C_{1-6}$ alkyl group, or a plurality of $R^3$s may be coupled to form an alicyclic hydrocarbon structure or heterocyclic structure having from 6 to 12 carbon atoms including carbon atoms to which the $R^3$s are bonded, and m stands for an integer of from 0 to 9.

5. A photoacid generator for chemical amplification resist material, the photoacid generator comprising a sulfonyldiazomethane compound as claimed in claim 1.

6. A chemical amplification resist material, comprising:
(A) a resin which changes its solubility in an alkali developer as a consequence of action of an acid; and
(B) a sulfonyldiazomethane compound as claimed in claim 1 which can generate an acid by exposure to radiation.

7. The resist material of claim 6, further comprising
(C) a compound which is other than component (B) and which can generate an acid by exposure to radiation.

8. The resist material according to claim 6, wherein said resin of component (A) has a substituent capable of changing the solubility in an alkali developer as a consequence of having the substituent removed by action of an acid.

9. The resist material according to claim 8, wherein said resin of component (A) is a polymer having a weight-average molecular weight of 3,000 to 100,000 and comprising a phenolic hydroxyl group wherein greater than 0 mole % but not greater than 80 mole %, on the average, of entire hydrogen atom of the phenolic hydroxyl group is replaced by said substituent capable of changing the solubility in an alkali developer as a consequence of having the substituent removed by action of an acid.

10. The resist material according to claim 9, wherein said resin of component (A) is a polymer comprising a repeating unit represented by formula (2a):

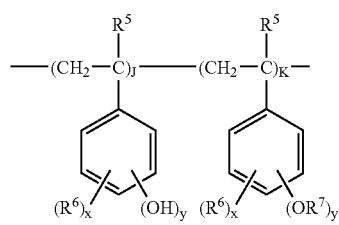

wherein the $R^5$s may be the same or different and each represents a hydrogen atom or a methyl group; the $R^6$s may be the same or different and each represents a linear, branched or cyclic $C_{1-8}$ alkyl group; x stands for 0 or a positive integer and y stands for a positive integer, satisfying $x+y \leqq 5$; the $R^7$s may be the same or different and each represents a substituent capable of changing solubility in an alkali developer as a consequence of having the substituent removed by action of an acid; J and K each independently stand for a positive integer, satisfying $0<K/(J+K)\leqq0.8$.

11. The resist material according to claim 8, wherein said resin of component (A) is a polymer having a weight-average molecular weight of 3,000 to 100,000; comprising a repeating unit based on acrylate and methacrylate in an amount exceeding 0 mole % but not greater than 50 mole % on average; comprising a repeating unit, containing the substituent capable of changing the solubility in an alkali developer as a consequent of having the substituent removed by action of an acid in an amount exceeding 0 mole % but not greater than 80 mole %, on the average, of the entire resin of component (A); and comprising a repeating unit of formula (2a'):

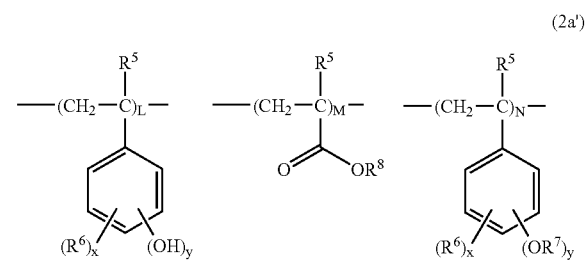

wherein the $R^5$s may be the same or different and each represents a hydrogen atom or a methyl group; the $R^6$s may be the same or different and each represents a linear, branched or cyclic $C_{1-8}$ alkali group; $R^7$ represents a substituent capable of changing the solubility in an alkali developer as a consequence of having the substituent removed by action of an acid; the $R^8$s may be the same or different and each represents a hydrogen atom or an acid-labile group with a proviso that at least part of the $R^8$s can change solubility in an alkali developer as a consequence of having the part removed by action of an acid; x stands for 0 or a positive integer and y stands for a positive integer, satisfying $x+y\leqq5$; L and M each independently stand for positive integers, and N stands for 0 or a positive integer, satisfying $0<M/(M+N+L)\leqq0.5$ and $0<(M+N)/(M+N+L)\leqq0.8$.

12. The resist material according to claim 8, wherein said resin of component (A) is a polymer having a weight-average molecular weight of 3,000 to 100,000; comprising a repeating unit based on indene and/or substituted indene in an amount exceeding 0 mole % but not greater than 50 mole % on average; comprising a repeating unit, containing a substituent capable of changing the solubility in an alkali developer as a consequence of having the substituent removed by action of an acid, in an amount exceeding 0 mole % but not greater than 80 mole % on average based on the entire resin of component (A);

and comprising a repeating unit of formula (2a''):

(2a'')

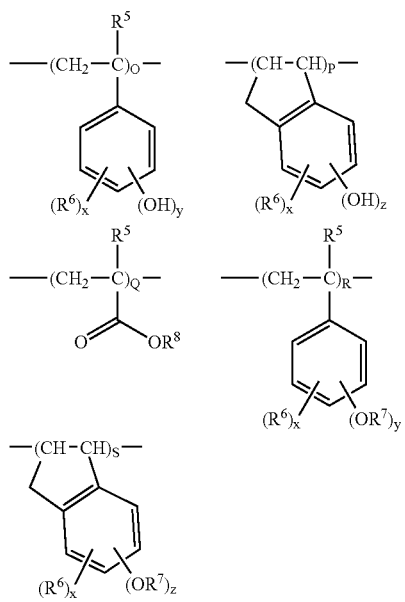

wherein the $R^5$s may be the same or different and each represents a hydrogen atom or a methyl group; the $R^6$s may be the same or different and each represents a linear, branched or cyclic $C_{1-8}$ alkali group; the $R^7$s may be the same or different and each represents a substituent capable of changing solubility in an alkali developer as a consequence of having the substituent removed by action of an acid; the $R^8$s may be the same or different and each represents a hydrogen atom or acid-labile group with a proviso that at least part of the $R^8$s can change solubility in an alkali developer as a consequence of having the part removed by action of an acid; x stands for 0 or a positive integer and y stands for a positive integer, satisfying $x+y \leq 5$; z stands for 0 or a positive integer satisfying $x+z \leq 4$; O and P each independently stand for positive integers and Q, R and S each independently stand for 0 or positive integers, satisfying $0<(P+S)/(O+P+Q+R+S) \leq 0.5$ and $0<(Q+R+S)/(O+P+Q+R+S) \leq 0.8$.

13. The resist material according to claim 8, wherein said substituent capable of changing solubility in an alkali developer by having the substituent removed by action of an acid is selected from the group consisting of a $C_{4-20}$ tertiaryl alkyl group, a trialkyl silyl group with each alkyl being a $C_{1-6}$ alkyl group, a $C_{4-20}$ oxoalkyl group, an aryl-substituted alkyl group having 7 to 20 carbons, and groups represented by formulas (4) to (7):

(4)

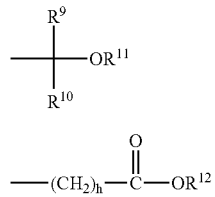

(5)

—$(CH_2)_h$—$\overset{O}{\underset{\|}{C}}$—$OR^{12}$

-continued (6)

(7)

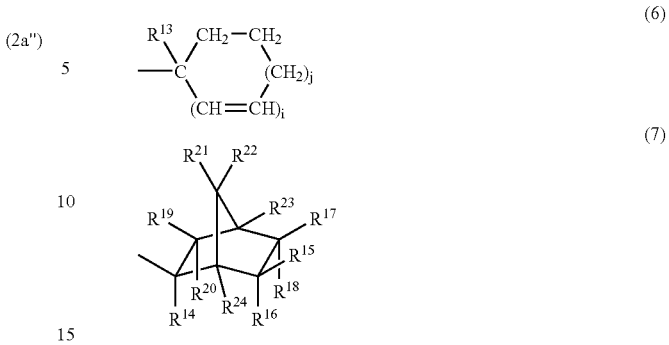

wherein $R^9$ and $R^{10}$ each represents a hydrogen atom or a linear, branched or cyclic $C_{1-18}$ alkyl group; $R^{11}$ represents a monovalent $C_{1-18}$ hydrocarbon group which may have a hetero atom; a pair of $R^9$ and $R^{10}$, $R^9$ and $R^{11}$, or $R^{10}$ and $R^{11}$ may form a ring, with a proviso that when the ring is formed, $R^9$, $R^{10}$ and $R^{11}$ each represents a linear or branched $C_{1-18}$ alkylene group; $R^{12}$ represents a $C_{4-20}$ tertiary alkyl group, a trialkysilyl group with each alkyl having a $C_{1-6}$ alkyl group, a $C_{4-20}$ oxoalkyl group, or a group represented by formula (4); h stands for an integer of 0 to 6; $R^{13}$ represents a linear, branched or cyclic $C_{1-8}$ alkyl group or a $C_{6-20}$ aryl group which may be substituted; i stands for 0 or 1, j stands for any one of 0, 1, 2 and 3, satisfying $2i+j=2$ or 3; $R^{14}$ is a linear, branched or cyclic $C_{1-8}$ alkyl group or a $C_{6-20}$ aryl group which may be substituted; and $R^{15}$ to $R^{24}$ each independently represents a hydrogen atom or a monovalent $C_{1-15}$ hydrocarbon group which may contain a heteroatom, or the $R^{15}$ to $R^{24}$ may form a ring with a proviso that when the $R^{15}$ to $R^{24}$ form a ring, the $R^{15}$ to $R^{24}$ each represents a divalent $C_{1-15}$ hydrocarbon group which may contain a heteroatom, or the $R^{15}$ to $R^{24}$ which are bonded to neighboring carbon atoms may form a double bond directly.

14. The resist material according to claim 6, further comprising (D) a basic compound.

15. The resist material according to claim 6, further comprising (E) an organic acid derivative.

16. The resist material according to claim 6, further comprising, as a component of a solvent, a propylene glycol alkyl ether acetate and/or an alkyl lactate.

17. A patterning process, comprising steps of:
applying the resist material as claimed in claim 6 onto a substrate to form a coating,
heating the coating,
exposing the coating to high energy radiation with a wavelength not greater than 300 nm or electron beam through a photomask, and
developing the exposed coating with a developer after an optional heat treatment.

18. A sulfonyldiazomethane compound represented by formula (1a'):

(1a')

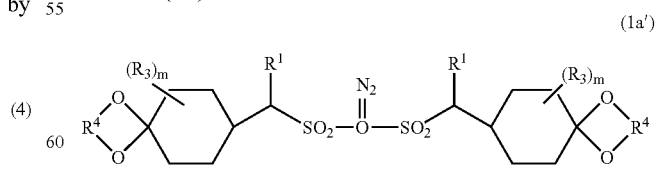

wherein the $R^1$s may be the same or different, and each represents a hydrogen atom or a linear, branched or cyclic, substituted or unsubstituted $C_{1-6}$ alkyl group; the $R^3$s may be the same or different and each represents a hydrogen atom or a linear, branched or cyclic, substituted or unsubstituted $C_{1-6}$ alkyl group, or a plurality of the $R^3$s may be coupled to form an alicyclic hydrocarbon structure or heterocyclic structure having from 6 to 12 carbon atoms including carbon atoms to which the $R^3$s are bonded; m stands for an integer of 0 to 9; and the $R^4$s may be the same or different and each represents a linear or branched $C_{2-6}$ alkylene group.

19. A sulfonyldiazomethane compound represented by formula (1a″):

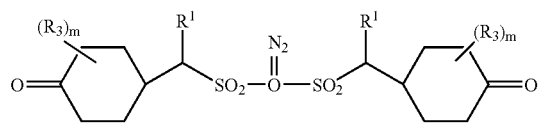

wherein the $R^1$s may be the same or different, and each represents a hydrogen atom or a linear, branched or cyclic, substituted or unsubstituted $C_{1-6}$ alkyl group; the $R^3$s may be the same or different and each represents a hydrogen atom or a linear, branched or cyclic, substituted or unsubstituted $C_{1-6}$ alkyl group, or a plurality of the $R^3$s may be coupled to form an alicyclic hydrocarbon structure or heterocyclic structure having from 6 to 12 carbon atoms including carbon atoms to which the $R^3$s are bonded, and m stands for an integer of from 0 to 9.

20. A sulfonyldiazomethane compound selected from the group consisting of the following compounds:

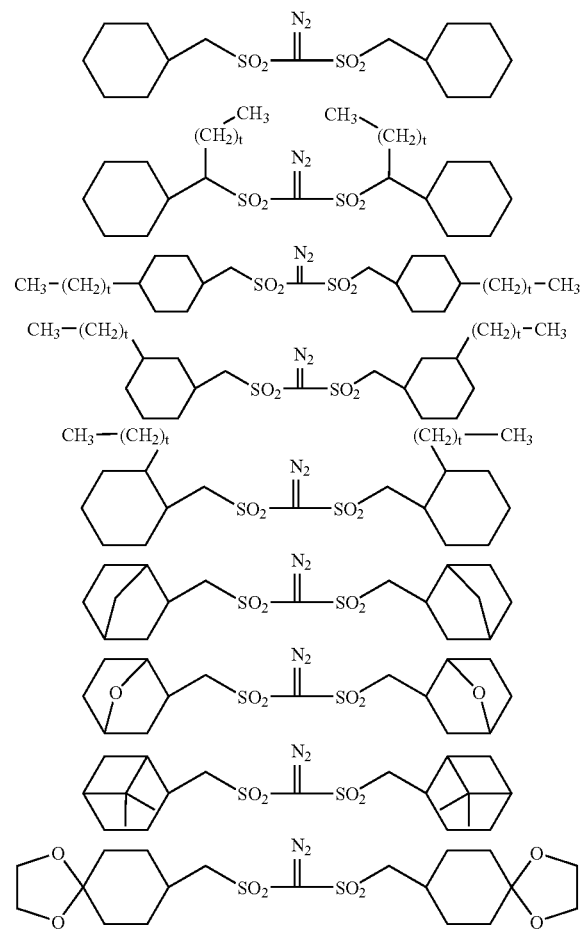

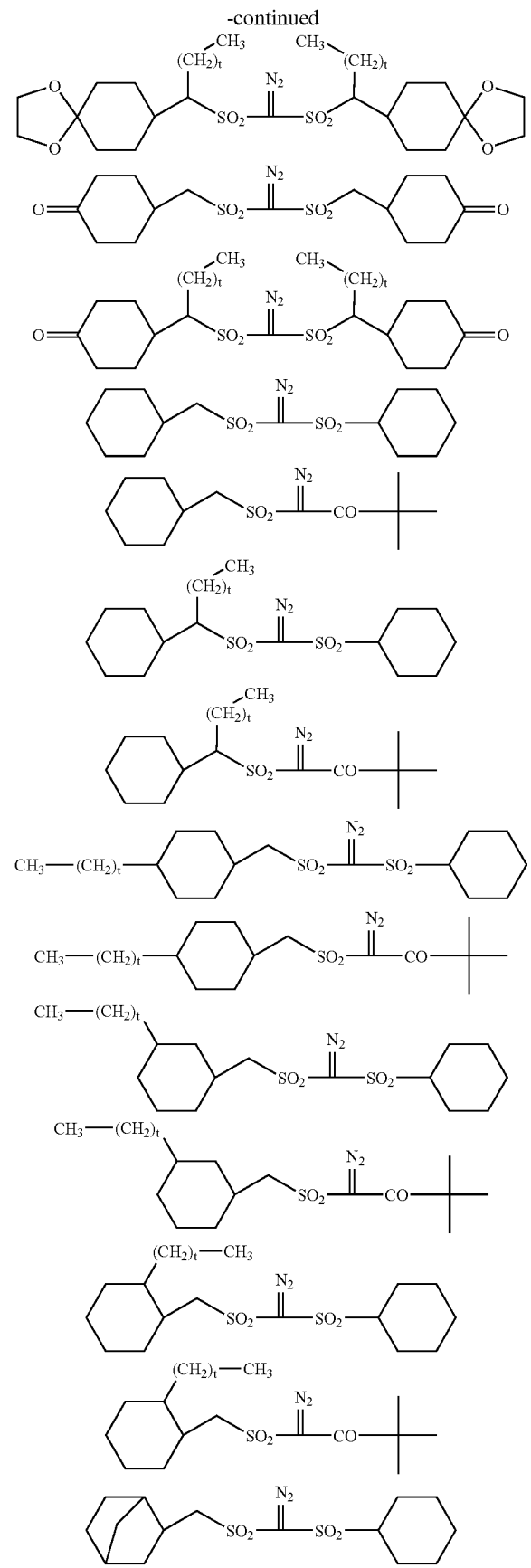

-continued
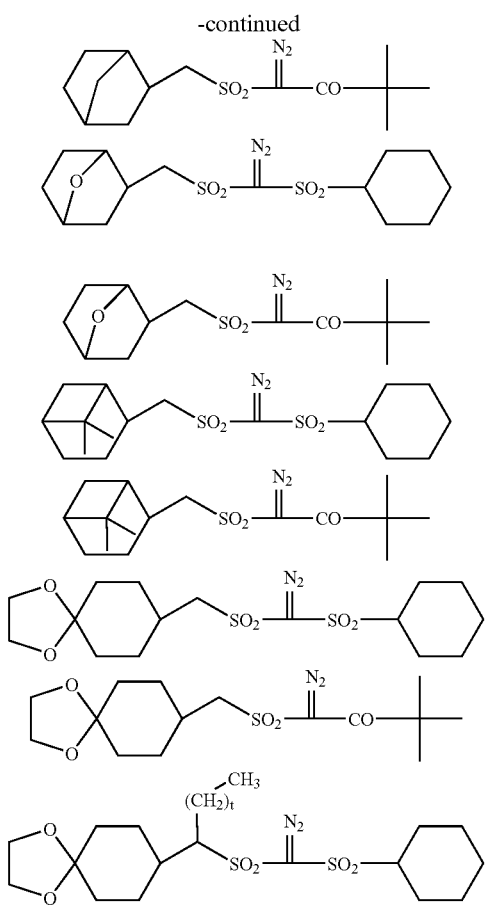
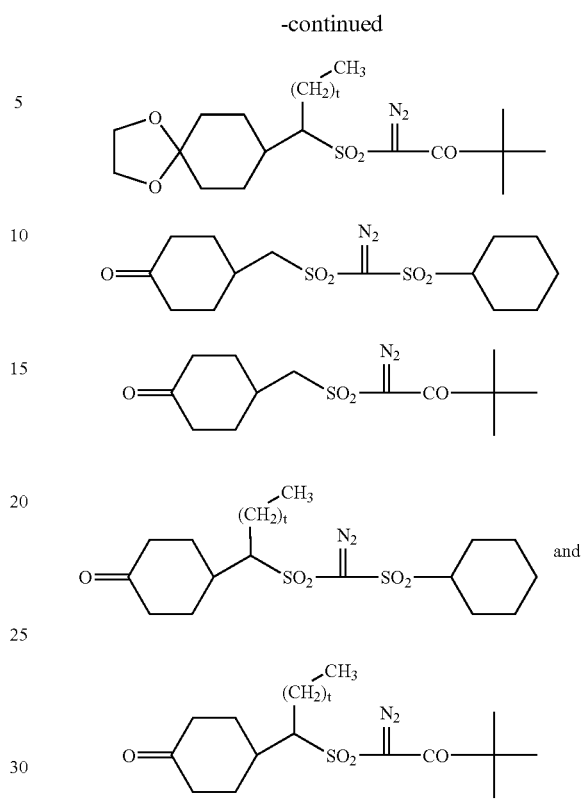
wherein t stands for an integer of from 0 to 5.
* * * * *

UNITED STATES PATENT AND TRADEMARK OFFICE
CERTIFICATE OF CORRECTION

| | | |
|---|---|---|
| PATENT NO. | : 7,282,316 B2 | Page 1 of 1 |
| APPLICATION NO. | : 10/929059 | |
| DATED | : October 16, 2007 | |
| INVENTOR(S) | : Kobayashi et al. | |

It is certified that error appears in the above-identified patent and that said Letters Patent is hereby corrected as shown below:

On the title page item [54]:

"SULFONYLDIAZOMETHANE COMPOUNDS, PHOTOACID GENERATOR,

RESIST MATERIALS AND PATTERNING USING THE SAME" should read

--SULFONYLDIAZOMETHANE COMPOUNDS, PHOTOACID GENERATOR,

RESIST MATERIALS AND PATTERNING PROCESS USING THE SAME--

Column 60

Line 17: "each represents" should read --each independently represents--

Column 60

Line 22: "each represents" should read --each independently represents--

Signed and Sealed this

Thirteenth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,282,316 B2  Page 1 of 1
APPLICATION NO. : 10/929059
DATED : October 16, 2007
INVENTOR(S) : Kobayashi et al.

It is certified that error appears in the above-identified patent and that said Letters Patent is hereby corrected as shown below:

On the title page item [54] and Column 1, lines 1-4:

"SULFONYLDIAZOMETHANE COMPOUNDS, PHOTOACID GENERATOR,

RESIST MATERIALS AND PATTERNING USING THE SAME" should read

--SULFONYLDIAZOMETHANE COMPOUNDS, PHOTOACID GENERATOR,

RESIST MATERIALS AND PATTERNING PROCESS USING THE SAME--

Column 60

Line 17: "each represents" should read --each independently represents--

Column 60

Line 22: "each represents" should read --each independently represents--

This certificate supersedes the Certificate of Correction issued May 13, 2008.

Signed and Sealed this

Seventeenth Day of June, 2008

JON W. DUDAS
*Director of the United States Patent and Trademark Office*